United States Patent
Hawthorne et al.

(10) Patent No.: US 7,462,149 B2
(45) Date of Patent: *Dec. 9, 2008

(54) METHOD AND APPARATUS FOR REMOTE BLOOD ALCOHOL MONITORING

(75) Inventors: Jeffrey Scott Hawthorne, Bennett, CO (US); Brian Kirby Phillips, Lakewood, CO (US); Michael Leonard Iiams, Littleton, CO (US); Williams James Roushey, III, Littleton, CO (US); Nolan James Farmer, Jr., Jamestown, CO (US)

(73) Assignee: Alcohol Monitoring Systems, Inc., Littleton, CO (US)

( * ) Notice: Subject to any disclaimer, the term of this patent is extended or adjusted under 35 U.S.C. 154(b) by 566 days.

This patent is subject to a terminal disclaimer.

(21) Appl. No.: 10/441,940

(22) Filed: May 19, 2003

(65) Prior Publication Data
US 2004/0236199 A1    Nov. 25, 2004

(51) Int. Cl.
*A61B 5/00* (2006.01)
(52) U.S. Cl. .................. 600/300; 600/301; 128/920
(58) Field of Classification Search ......... 600/300–301, 600/309, 353, 364, 583; 436/68, 132; 422/84; 128/920
See application file for complete search history.

(56) References Cited

U.S. PATENT DOCUMENTS

| | | | | |
|---|---|---|---|---|
| 4,173,971 A | * | 11/1979 | Karz | ......................... 600/515 |
| 4,749,553 A | * | 6/1988 | Lopez et al. | .................. 422/84 |
| 4,868,545 A | * | 9/1989 | Jones | ....................... 340/573.1 |
| 4,916,435 A | * | 4/1990 | Fuller | ...................... 340/573.4 |

(Continued)

FOREIGN PATENT DOCUMENTS

WO    WO-02/12883    *    2/2002    ................. 33/497

OTHER PUBLICATIONS

Michael C. Astorino, Office Action, Oct. 4, 2004, U.S. Appl. No. 10/441,960.

(Continued)

*Primary Examiner*—Max Hindenburg
*Assistant Examiner*—Rene Towa
(74) *Attorney, Agent, or Firm*—Merchant & Gould P.C.; Stanley J. Gradisar

(57) ABSTRACT

A tamper proof transdermal alcohol content monitoring device is made up of analog and digital sides which are securely attached to the human subject to be monitored. The analog side has a sampling circuit which draws a measured insensible skin perspiration sample from the skin of the subject and measured with an electrochemical fuel cell. A distance measurement of the device from the skin of the subject and temperature of the sample are monitored along with the transdermal alcohol content, and converted to digital signals which are transmitted to a modem when the monitor is in proximity to the modem. The signals are stored in the modem and uploaded to a central monitoring station. Automatic alerts may be sent from the central monitoring station to a supervising agency. The supervising agency may also access the information through secured dedicated websites via the Internet.

34 Claims, 12 Drawing Sheets

U.S. PATENT DOCUMENTS

| | | | | |
|---|---|---|---|---|
| 4,999,613 | A * | 3/1991 | Williamson et al. | 340/573.4 |
| 5,033,293 | A * | 7/1991 | Honma et al. | 73/118.1 |
| 5,220,919 | A * | 6/1993 | Phillips et al. | 600/345 |
| 5,303,575 | A * | 4/1994 | Brown et al. | 73/23.3 |
| 5,724,025 | A | 3/1998 | Tavori | 600/300 |
| 5,836,993 | A * | 11/1998 | Cole | 607/59 |
| 6,024,699 | A | 2/2000 | Surwit et al. | 600/300 |
| 6,409,675 | B1 * | 6/2002 | Turcott | 600/508 |
| 6,443,890 | B1 | 9/2002 | Schulze et al. | 600/300 |
| 6,524,239 | B1 | 2/2003 | Reed et al. | 600/300 |
| 6,726,636 | B2 * | 4/2004 | Der Ghazarian et al. | 600/532 |
| 6,805,667 | B2 * | 10/2004 | Christopherson et al. | 600/300 |
| 7,051,120 | B2 * | 5/2006 | Greene et al. | 709/250 |
| 2002/0156650 | A1 * | 10/2002 | Klein et al. | 705/2 |
| 2003/0126593 | A1 * | 7/2003 | Mault | 725/10 |

OTHER PUBLICATIONS

Michael C. Astorino, Office Action, Jun. 30, 2005, U.S. Appl. No. 10/441,960.

Michael C. Astorino, Office Action, Jan. 24, 2006, U.S. Appl. No. 10/441,960.

Michael C. Astorino, Office Action, Sep. 11, 2006, U.S. Appl. No. 10/441,960.

Michael C. Astorino, Interview Summary, Jan. 3, 2007, U.S. Appl. No. 10/441,960.

Michael C. Astorino, Notice of Allowability, Apr. 23, 2007, U.S. Appl. No. 10/441,960.

Michael C. Astorino, Notice of Allowability, Aug. 9, 2007, U.S. Appl. No. 10/441,960.

* cited by examiner

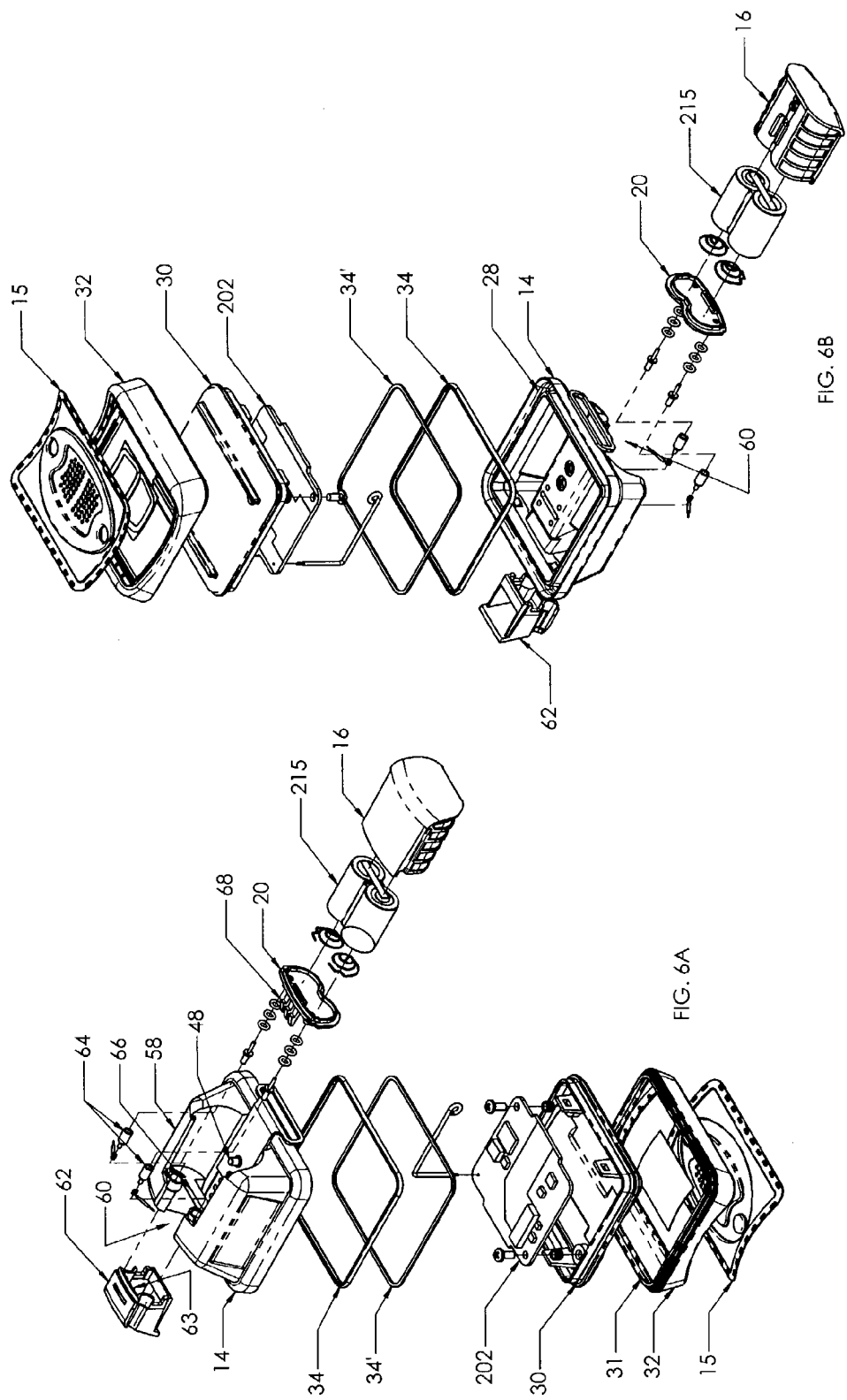

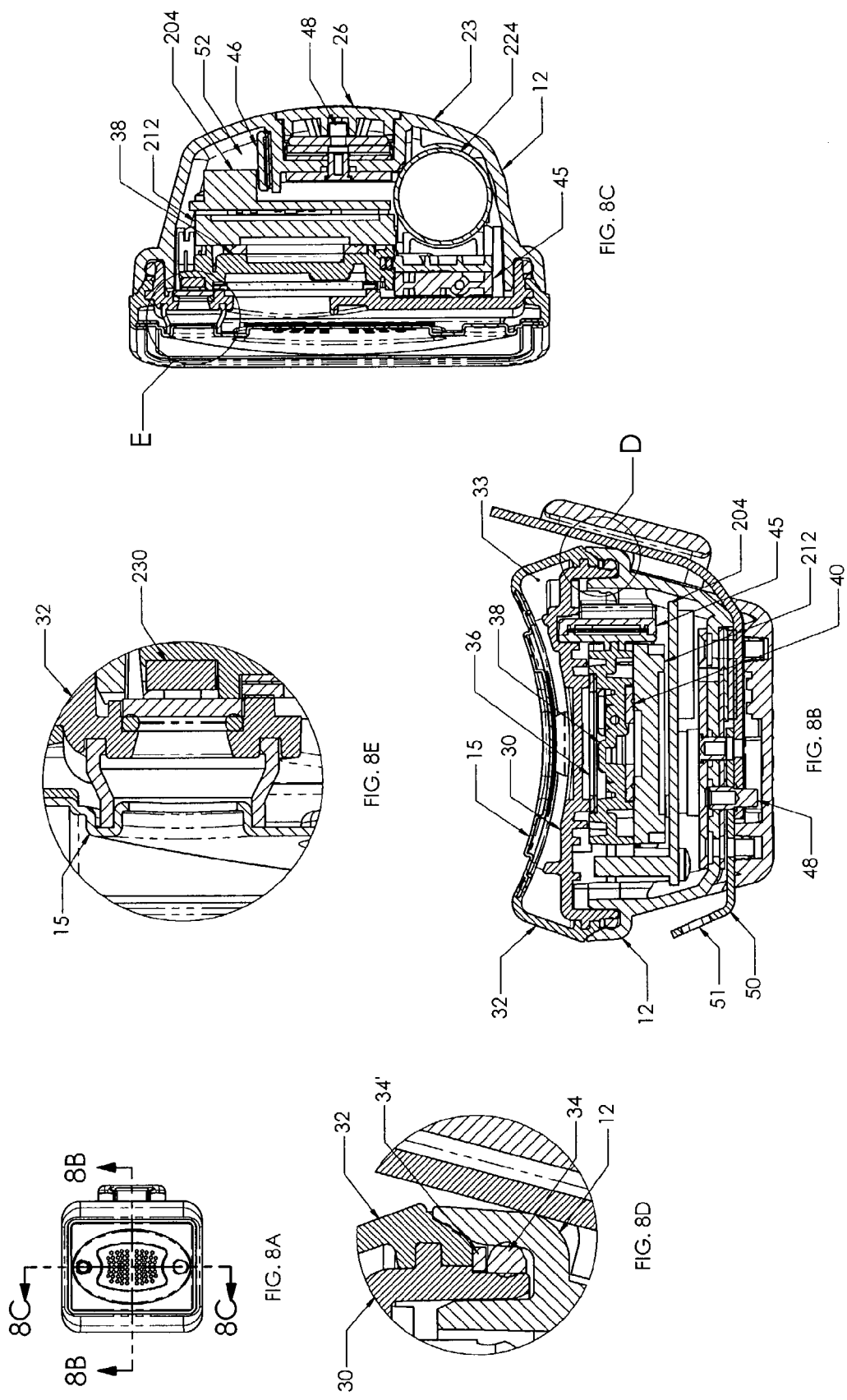

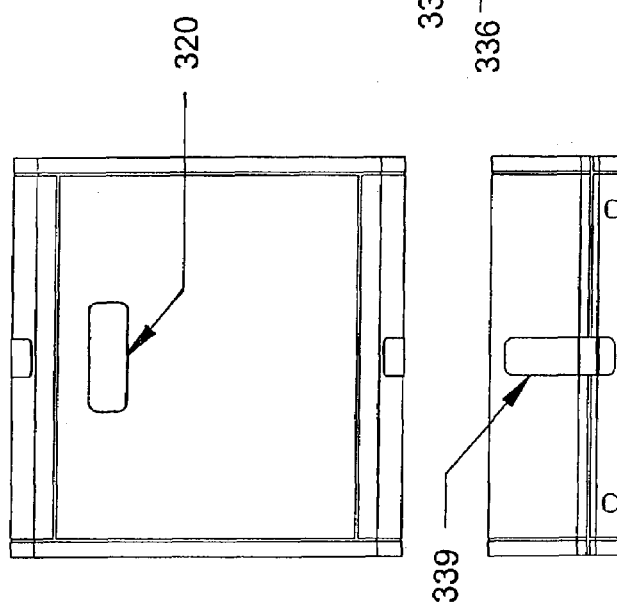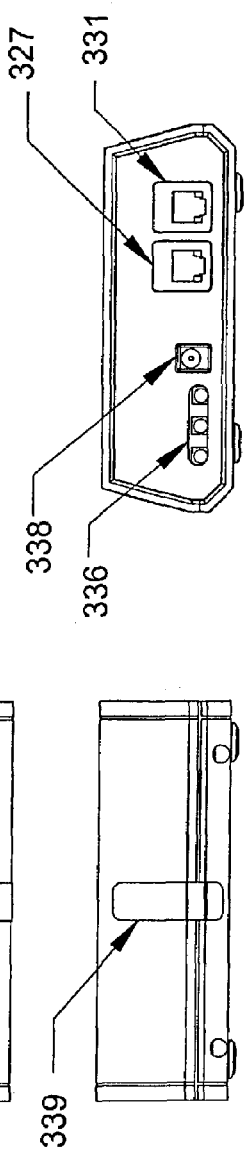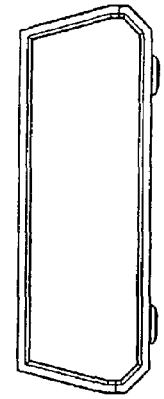

US 7,462,149 B2

METHOD AND APPARATUS FOR REMOTE BLOOD ALCOHOL MONITORING

CROSS REFERENCE TO RELATED APPLICATION

This application is related to a co-pending patent application Ser. No. 10/441,960 by Hawthorne et al. titled "BIO-INFORMATION SENSOR MONITORING SYSTEM AND METHOD" and filed on the same day herewith, which is owned by the same assignee of this invention.

FIELD OF THE INVENTION

This invention relates to a blood alcohol monitoring system, and more particularly, relates to an improved non-invasive method and apparatus for transdermal monitoring of blood alcohol levels.

BACKGROUND OF THE INVENTION

Reference is made to U.S. Pat. No. 5,220,919 titled "BLOOD ALCOHOL MONITOR" and European Patent No. EPO 623001B1 titled "BLOOD ALCOHOL MONITOR", both owned by the assignee of this invention and both are hereby incorporated herein by reference.

Individuals on probation, parole, or in alcohol treatment programs may be prohibited from consuming alcohol, and many federal, state, and local law enforcement agencies require testing to ensure participants in court ordered programs remain alcohol free. In general, present-generation remote alcohol monitoring devices used in probation, parole, and treatment settings are fixed-location breath-testing devices that utilize voice or video identification of the participant. If a subject tests positive for alcohol, the monitoring device then sends a message alerting the monitoring center of a violation by the subject, and the monitoring center then sends an alert message to the subject's supervising agency or dedicated administrator.

As alcohol is ingested orally, it is absorbed into the body's blood and distributed throughout the body via the circulatory system. Alcohol is eliminated from the body by two mechanisms: metabolism and excretion. Metabolism accounts for the removal of greater than 90% of the alcohol consumed, removing it from the body via oxidation of the ethyl alcohol molecule to carbon dioxide and water primarily in the liver. The remaining alcohol is excreted unchanged wherever water is removed from the body—breath, urine, perspiration, and saliva. Although excretion accounts for less than 10% of the eliminated alcohol, it is significant because unaltered alcohol excretion permits an accurate measurement of alcohol concentration in the body by way of both breath analysis and insensible skin perspiration. Insensible skin perspiration is the vapor that escapes through the skin through sweating. The average person will emit approximately one liter of insensible skin perspiration each day. This perspiration can be used to obtain a transdermal measurement of blood alcohol concentration, referred to as Transdermal Alcohol Concentration ("TAC").

Transdermal monitoring of blood alcohol levels is accomplished by taking percentage measurements of alcohol contained in the air vapor that is expelled through human skin. A monitoring device is attached to the skin to capture the air and measure the alcohol. There are numerous advantages to transdermal monitoring, as opposed to breath alcohol testing, including, but not limited to, the ability to take readings at any time without the knowledge of the subject, consistent and continuous testing (unlike breath alcohol testing where a subject breathing incorrectly into the testing device can cause inaccurate results), and the ability to convert such readings into electrical signals that can be transmitted to a central monitoring station.

However, there is a continuing need for a remote alcohol monitoring system which can be conveniently placed on the subject that can carry out TAC measurements at selected time intervals as well as at random times. There is also a need for a remote alcohol monitoring system that will compensate for the effects of temperature changes on TAC readings, is tamper-proof, and virtually impossible for the subject to remove without triggering an alarm. Still further, there is also a need to be able to download the TAC measurements to a monitoring station without requiring any actions on the part of the subject being monitored, eliminating the need for the subject to personally report to a central monitoring station or probation officer, or connect the monitoring device to a telephone line to download and transmit data to a monitoring station. The present invention meets these and other needs in the art.

BRIEF DESCRIPTION OF THE DRAWINGS

FIG. 6A shows an exploded perspective view of the digital side of the monitor device shown in FIG. 4 in an embodiment of the present invention.

FIG. 6B shows another exploded perspective view of the digital side of the monitor device shown in FIG. 4 but reversed 180° with respect to that shown in FIG. 6A in an embodiment of the present invention.

FIG. 8A shows a front view in elevation of the analog side of the monitor device shown in FIG. 4 in an embodiment of the present invention.

FIG. 8B shows a cross-sectional view taken about line 8B of FIG. 8A in an embodiment of the present invention.

FIG. 8C shows a cross-sectional view taken about line 8C of FIG. 8A in an embodiment of the present invention.

FIG. 8D shows a detailed view taken at D of FIG. 8B in an embodiment of the present invention.

FIG. 8E shows another detailed view taken at E of FIG. 8C in an embodiment of the present invention.

FIGS. 13A-13D show a top view and three elevation views of the modem in an embodiment of the present invention.

DETAILED DESCRIPTION OF THE INVENTION

Figure 1:
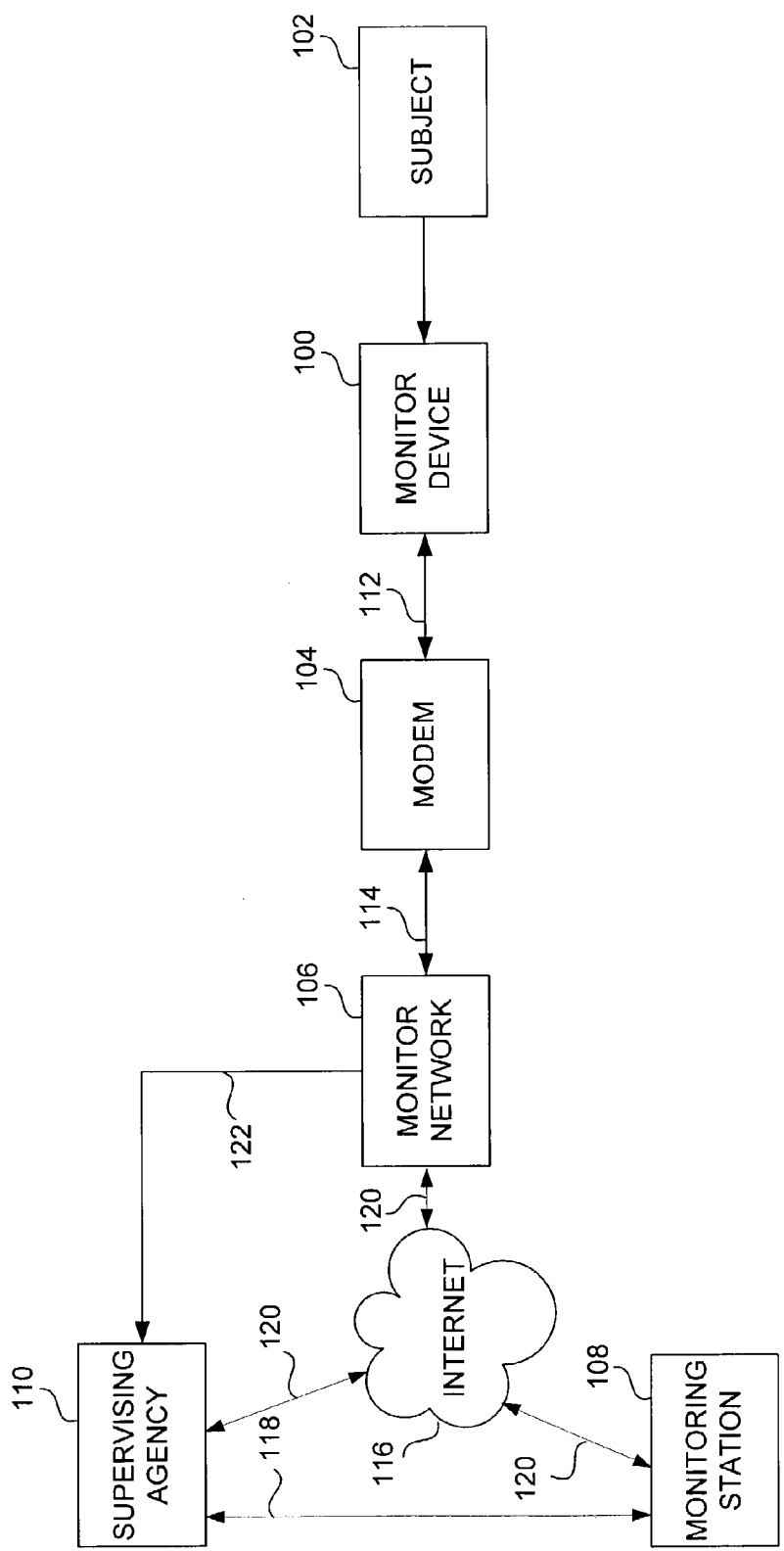
FIG. 1 shows a block diagram of a preferred form of monitoring system in an embodiment of the present invention.

Referring now to the Figures, in which like reference numerals refer to structurally and/or functionally similar elements thereof, FIG. 1 shows by way of illustrative example a system block diagram of the method and apparatus for remote blood alcohol monitoring between a human Subject 102 and a Monitoring Station 108. The preferred form of Monitor Device 100 weighs about eight ounces, is waterproof, and designed to handle the stress of everyday activity, and can be worn under any conditions, including bathing and swimming. Monitor Device 100 is attached to the Subject 102 being monitored in a manner to be described. Once Monitor Device 100 is in place, it cannot be removed without triggering a tamper alarm, which is recorded in Monitor Device 100. In addition, there are a number of anti-tamper features designed into Monitor Device 100 to ensure that the TAC readings taken are from Subject 102, and accurately represent the blood alcohol level of Subject 102 and not some other person. Though this discussion focuses on one Subject 102, one skilled in the art will recognize that many Monitor Devices 100 may be attached to many Subjects 102 at the same time over a broad geographic area, and all may be monitored by Monitoring Station 108, which is the intended purpose of the invention. Likewise, there may be multiple Monitor Networks 106 and Monitoring Stations 108 that manage additional Subjects 102 in diverse geographic locations.

Monitor Device 100 will take TAC readings that are time stamped at predetermined or random intervals twenty-four hours a day, seven days a week, 365 days a year, without active participation by Subject 102. Testing schedules may range from as frequent as every 30 minutes or as infrequent as once per day. Monitor Device 100 collects TAC data from Subject 102 regardless of the location or activity of Subject 102. While commuting, at work, at home, during recreation, in the shower, or sleeping, Subject 102 is passively monitored, allowing for continual, effective monitoring while Subject 102 maintains a normal routine. Subject 102 typically does not know when the sampling will occur. Typical existing alcohol monitoring programs that have used other means of testing subjects for alcohol will likely see an increase in the number of program positives utilizing the present invention. This is a result of the continuous monitoring, rather than the pre-arranged, specific testing times typical of current monitoring programs. Continuous monitoring eliminates the ability for subjects to manipulate their drinking patterns to avoid detection.

TAC readings are taken as scheduled without the participation of Subject 102, with the data uploaded at scheduled time intervals to Modem 104, or immediately if a positive drinking event or a tamper is detected and Modem 104 is in range. Typically, Modem 104 would be placed at the residence of Subject 102, and Subject 102 is merely required to periodically be in proximity to Modem 104 for the purpose of allowing automatic transmission of TAC measurements taken by Monitor Device 100 over a period of time. Subject 102 comes within range of Modem 104, typically within about ten to twenty feet, on a periodic basis, such as once per day, to allow the automatic transmission to take place. Different hardware components may increase or decrease the range at which the automatic transmission will take place. Subject 102 may rise and leave for work, return home, and remain at home until the next day when it is time to leave for work again. When Monitor Device 100 is in range and the timer indicates that it is time to communicate with Modem 104, Monitor Device 100 will transfer to Modem 104 through radio frequency ("RF") signals through bi-directional RF Communication Link 112 all the TAC readings, tamper indicators, error indicators, diagnostic data, and any other data stored in Monitor Device 100 regarding Subject 102. Modem 104 also can transmit operational information, such as monitoring schedules and reporting schedules in the form of RF signals back to Monitor Device 100 over bi-directional RF Communication Link 112.

Modem 104 stores the data contained in the RF signals received from Monitor Device 100 for transmission to Monitor Network 106. After receiving all of the information from Monitor Device 100, Modem 104 will check the stored data for any TAC readings, tampers, errors, or diagnostic data. Any one of these, or a trigger from a predetermined time interval, will cause Modem 104 to establish a connection over Communication Link 114 with Monitor Network 106. Once a connection is established, Monitor Network 106 validates the identity of Modem 104 and authenticates the data before it is stored. Once validated, Modem 104 will transfer all of the TAC readings, tampers, errors, diagnostic data, and any other data stored to a web-hosted database server at Monitor Network 106 where all data is permanently stored. Monitor Network 106 then analyzes the data received and separates and groups the data into a number of separate categories for reporting to monitoring personnel at Monitoring Station 108. The data can then be accessed by the monitoring personnel through the use of secured dedicated websites through the Internet 116 and Internet Connection 120 to Monitor Network 106. When Monitor Network 106 analyzes the data received, an automatic alert, based upon a rules-based database, may be sent directly from Monitor Network 106 to a call center at Supervising Agency 110 over Communication Link 122, or to an individual previously designated by Supervising Agency 110, when a specific alert, or combination of alerts, are received. The alert may be an e-mail, a fax, or a page to a previously provided number. Communication Link 122 may be a wire or wireless connection.

Monitor Network 106 may be located at Monitoring Station 108, or in a separate location. Monitoring personnel at Monitoring Station 108 have access to all of the data gathered on all of the Subjects 102. Supervising personnel at the call center of Supervising Agency 110, however, only have access to those Subjects 102 that are associated with Supervising Agency 110.

Monitoring Station 108 may automatically or periodically transmit data received from Modem 104 via Monitor Network 106 to one or more persons at Supervising Agency 110 who are assigned to monitor Subject 102, such as a parole officer, probation officer, case worker, or other designated person or persons in charge of enrolling Subject 102 and monitoring the data being collected on Subject 102. Only one Supervising Agency 110 is shown for simplicity, but one skilled in the art will recognize that many Supervising Agencies 110 may be accessing Monitor Network 106 at any given time. A connection is established with Supervising Agency 110 through Communication Link 118. Typically this connection is accomplished via the telephone system through a wire or wireless link, and may connect to a pager or cellular phone of the designated person. Designated personnel at Supervising Agency 110 may also access Monitor Network 106 through the use of secured dedicated websites through the Internet 116 and Internet Connection 120 to Monitor Network 106. Monitor Network 106 web software allows Supervising Agency 110 the ability to track Subject 102 compliance in a manner most feasible to them, and can be defined to fit the needs of both small and large programs. Each Supervising Agency 110 may customize the frequency of monitoring and the method of notification for alerts that they want to receive from Monitor Network 106. Alerts may be categorized by the type and severity of alert, allowing each Supervising Agency 110 to prioritize and better categorize a response (i.e., a low battery warning versus a possible alcohol violation).

Each Supervising Agency 110 has its own separate data storage area on the database server at Monitor Network 106 so that representatives from each Supervising Agency 110 can retrieve the secure data they need when they need it. The method and system of the present invention will work in conjunction with existing monitoring agencies that are experienced at managing alcohol offenders.

The method and apparatus for remote blood alcohol monitoring of the present invention has many advantages and benefits over existing methods and apparatus, including, but not limited to, no collection of body fluids (blood, breath, urine) that require special gathering, handling, or disposal considerations; no waiting for laboratory test results; there is no need for the subject to travel to a test center; continuous 24/7/365 monitoring and data collection from any location; no subject, agency official, or laboratory intervention—only passive participation on the part of the subject; the monitoring device is light weight and can be hidden from normal view; tamper-resistant technology ensures accurate readings representative of the subject being monitored; advanced technology utilizing microprocessors, encrypted data links, and secure data storage and retrieval; the ability for monitored subjects to maintain normal daily routines, including work, counseling, community service, family obligations, and recreation; and easy, web-based, secure access for the monitoring agency to each subject's data.

Figure 2:
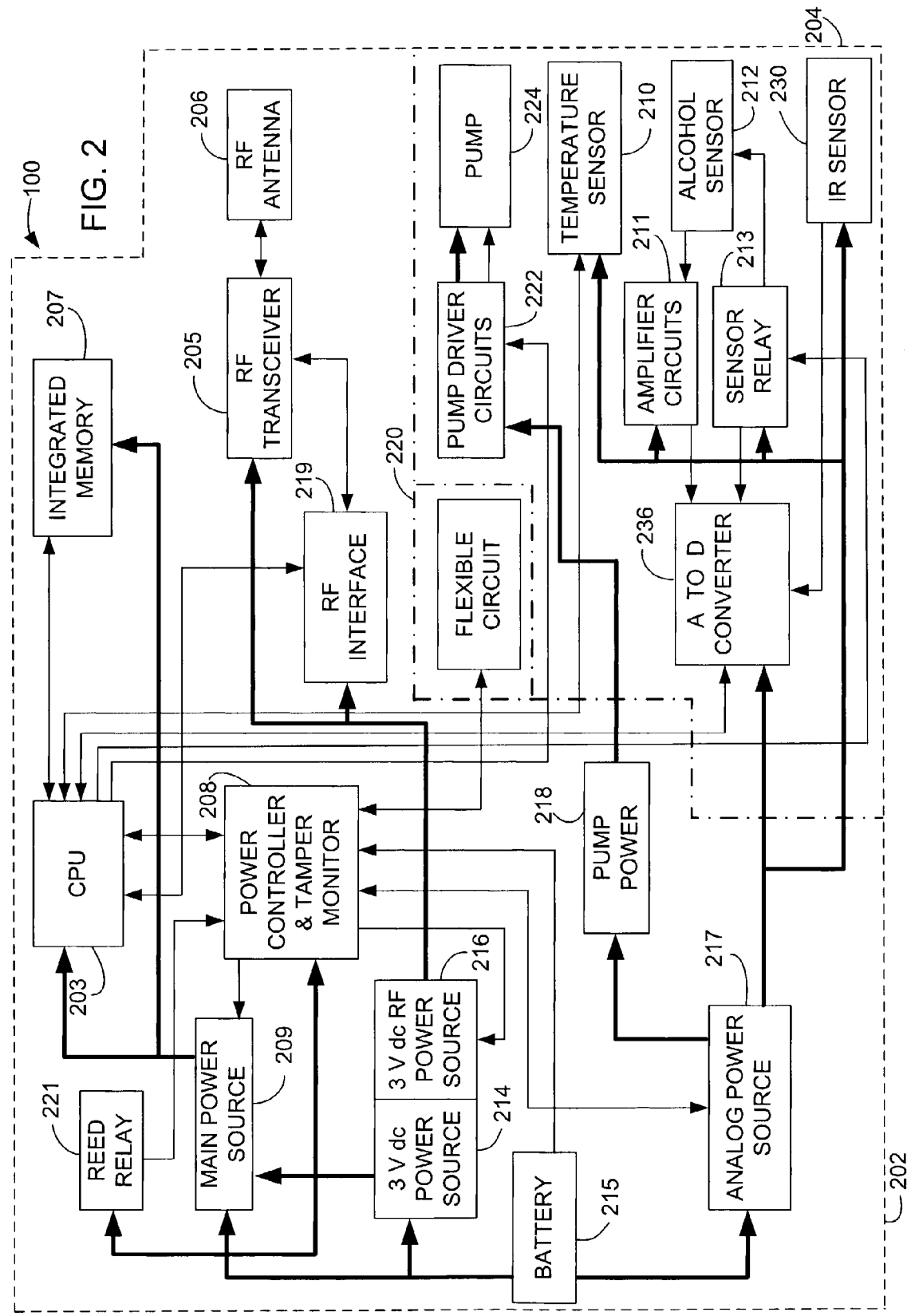
FIG. 2 shows a block diagram of the sensing circuit of the monitor device in an embodiment of the monitoring system of the present invention.

FIG. 2 shows a block diagram of an embodiment of Monitor Device 100. Referring now to FIG. 2, thicker arrows represent power circuits, and thinner arrows represent signal circuits. Monitor Device 100 is made up of two separate circuit boards referred to as Digital Board 202 and Analog Board 204 that are connected together by a Flexible Circuit 220 which also serves as a tamper strap.

Digital Board 202 contains a micro-controller that functions as a Power Controller And Tamper Monitor 208. Power Controller And Tamper Monitor 208 controls all of the power in Monitor Device 100. When Battery 215 is inserted into Monitor Device 100, Power Controller And Tamper Monitor 208 is activated by the 3 V dc Power Source 214, and Monitor Device 100 operates at a 3 volt level. Once Power Controller And Tamper Monitor 208 is initialized and running it will turn on the main power to Monitor Device 100 by activating the Main Power Source 209. Power Controller And Tamper Monitor 208 will now operate at a 5 volt level with the rest of the circuits.

Another function of Power Controller And Tamper Monitor 208 is to monitor the output power level of Battery 215 that operates Monitor Device 100. This is accomplished by running the raw battery voltage through a resistive voltage divider and then connecting it directly to Power Controller And Tamper Monitor 208. Power Controller And Tamper Monitor 208 also power controls the power to Analog Board 204 through the Analog Power Source 217. Analog Power Source 217 in turn provides power to Pump Power 218 which powers the pump circuits, so that the pump circuits are not powered up unless Analog Board 204 is turned on.

Another function of Power Controller And Tamper Monitor 208 is to provide a real time clock that may set the increments of time that Monitor Device 100 is turned off before turning back on. The time and date are downloaded to Central Processing Unit ("CPU") 203 from Modem 104 and are then communicated to Power Controller And Tamper Monitor 208, which will then keep track of the time and date and automatically turn on Main Power Source 209 at scheduled times, which can be programmed by CPU 203. Power Controller And Tamper Monitor 208 allows Monitor Device 100 to turn itself on and off to conserve battery life, and allows external stimulus events to turn on power to Monitor Device 100.

The tamper control portion of Power Controller And Tamper Monitor 208 monitors all of the inputs that can cause Monitor Device 100 to wake up due to some kind of a tamper condition. The first condition occurs if a magnet is passed near Reed Relay 221. Passing a magnet near Reed Relay 221 is a method that monitoring personnel employ to wake up Monitor Device 100 in order to take a TAC reading at an unscheduled time. However, Subject 102 may attempt to repeatedly pass a magnet near Reed Relay 221 in order to wear the battery down. Therefore, even when activated by monitoring personnel, any such activation of Monitor Device 100 is still processed as a tamper. Monitoring personnel can note in the records that the tamper event recorded as a result of their actions was a manual turn on, and not a tamper, and prevent any notifications from being sent to Supervising Agency 110.

Passing a magnet near Reed Relay 221 will cause it to open and close, creating a pulsing effect at the tamper monitoring input. When Power Controller And Tamper Monitor 208 detects this pulsing input it will immediately turn on Main Power Source 209 and activate Monitor Device 100. A tamper event record is recorded, and the procedure to take a TAC reading is initiated. A temperature reading and a distance reading are also taken. Monitor Device 100 then checks to see if it is within range of Modem 104. If so, then the communication and transmission procedure is initiated.

The tamper control portion of Power Controller And Tamper Monitor 208 also monitors a continuous signal that is being passed through Flexible Circuit 220 and Analog Board 204 and back to the tamper control portion. If this signal is interrupted, then Power Controller And Tamper Monitor 208 will immediately activate Main Power Source 209 and Monitor Device 100 will proceed as outlined above.

As mentioned above, Digital Board 202 also contains CPU 203 which is a stand alone processor which typically has no internal memory component. In another embodiment of the invention, CPU 203 and Integrated Memory 207 may be combined together in the same chip. CPU 203 retrieves all of its instructions and data from Integrated Memory 207, which is used for both program memory and data storage memory.

Integrated Memory 207 is divided internally into several different memory segments. There is a small segment of the memory dedicated to the boot strap program. The boot strap program is used to initialize Monitor Device 100 when power is first applied. The boot strap program is a very basic program that will initialize CPU 203 and then check the validity of the main operating program that is stored in a larger section of Integrated Memory 207. The boot strap program also has the capability of establishing communications through RF Communication Link 112 if the main program is not valid.

The RF link between Monitor Device 100 and Modem 104 is established through the use of a serial to RF Transceiver 205 and RF Antenna 206. CPU 203 will command Power Controller And Tamper Monitor 208 to turn on 3 V dc RF Power Source 216. Power Controller And Tamper Monitor 208 will then activate 3 V dc RF Power Source 216 and supply all the RF components with 3 volts. CPU 203 is connected to RF Transceiver 205 through RF Interface 219 which allows the 5 volt serial signal from CPU 203 to be converted to the proper voltage (3 volts) for the RF transceiver circuits. By establishing RF Communication Link 112 the main program can then be downloaded into Monitor Device 100 by Modem 104 if required. Once the boot strap program has verified that the main program is valid, it will then switch operation to the main program segment stored in Integrated Memory 207 instead of establishing RF Communication Link 112.

Analog Board 204 contains a serial programmable chip Analog to Digital ("A to D") Converter 236. This is a programmable chip in that it allows for amplifier gain to be applied to the signals that are being monitored thorough the use of internal Amplifier Circuits 211 and software stored in Integrated Memory 207, instead of using external hardware to amplify the signals. CPU 203 can then use the software to change the gain of all the A to D channels at any time. A to D Converter 236 is used to convert data created by Alcohol Sensor 212, Infrared ("IR") Sensor 230, and Sensor Relay 213 into digital data. These signals are input to A to D Converter 236 in analog form and are then converted to a digital signal and communicated through a serial link to CPU 203. Alcohol Sensor 212 is a passive electrochemical fuel cell. The output of Alcohol Sensor 212 is an electrical current which is proportional to the amount of alcohol present in the vapor sample. IR Sensor 230 measures the distance between Monitor Device 100 and the skin of Subject 102 to confirm that Monitor Device 100 has not been removed, or that a barrier has not been placed between the skin of Subject 102 and Monitor Device 100, such as plastic wrap, tape, paper, aluminum foil, playing cards, and the like. Sensor Relay 213 keeps Alcohol Sensor 212 shorted, and only opens it when a reading is being taken.

Analog Board 204 also contains serial Temperature Sensor 210. Temperature Sensor 210 measures temperature in degrees Celsius and transmits temperature readings through a serial link to CPU 203. A low temperature reading may indicate that Monitor Device 100 has been removed from the limb of Subject 102. Normally, the skin temperature of Subject 102 will constantly fluctuate up and down over time. A period of fairly constant temperature readings my be an indication that a barrier has been placed between the skin and Monitor Device 100. Temperature readings from Temperature Sensor 210 combined with distance readings from IR Sensor 230 are evaluated together to determine a tamper condition. Temperature readings are also used to adjust the TAC readings as discussed immediately below.

The last items on Analog Board 204 are Pump Driver Circuits 222 and Pump 224. CPU 203 will activate Pump 224 in the process of taking a reading. Pump 224 draws a consistent and predetermined amount of air across Alcohol Sensor 212, which measures the amount of alcohol present in the air sample. The amount of time that Pump 224 is activated is strictly controlled by CPU 203 in order to control the consistency of each sample taken. When the predetermined amount of time has expired, CPU 203 will turn off Pump 224. CPU 203 will then monitor Alcohol Sensor 212. Once the peak voltage from the alcohol sensor has been recorded, CPU 203 will then calculate the approximate TAC reading for the peak voltage recorded and store that information in Integrated Memory 207 for later retrieval by Modem 104.

Each Monitor Device 100 must be calibrated through a characterization process before it can be used to monitor a Subject 102. The characterization process takes several hours. In a controlled environment, air samples of known alcohol concentrations are introduced into the sample chambers of each Monitor Device 100 at six different temperatures. The voltage generated by Alcohol Sensor 212 is then recorded. Alcohol concentrations of 0.00%, 0.02%, 0.05%, and 0.08% are used in the characterization process. Thus, a table is created for each Monitor Device 100 having 24 separate values. An example of a characterization data table for a particular Monitor Device 100 is shown below. No two Monitor Devices 100 will have the same characterization table due to the variances of all of the assembled components. In the table below, the temperatures are listed across the top row of the table and the alcohol concentrations supplied are shown in the far left column. The resulting voltages from the Monitor Device 100 being characterized are shown in the table matrix corresponding to each sample and temperature.

The gain shown is the software gain that CPU 203 will use for each reading when Monitor Device 100 is operating on Subject 102. The gain is determined for each Monitor Device 100 during the characterization process, and will also vary from device to device. The first step in the characterization process is to heat Monitor Device 100 to the maximum temperature and allow it to settle in at that temperature. The gain is then set to a default value of 8. The maximum allowable sample (0.08%) is then introduced to Monitor Device 100. The resulting Alcohol Sensor 212 voltage is measured, and this voltage must be less than the maximum allowable voltage for Monitor Device 100. If it is, then the gain is increased and the test is repeated until the maximum allowable voltage is exceeded. Once the maximum allowable voltage has been exceeded, the gain is set back one level to ensure that the maximum allowable voltage will not be exceeded.

| Characterization Table | | | | | | |
| --- | --- | --- | --- | --- | --- | --- |
| %/Celsius | 15 | 21 | 27 | 33 | 39 | 45 |
| 0.00 | 0.18 | 0.36 | 0.34 | 0.36 | 0.40 | 0.52 |
| 0.02 | 0.54 | 0.82 | 1.08 | 1.04 | 1.14 | 1.24 |
| 0.05 | 1.10 | 1.98 | 2.14 | 2.20 | 2.26 | 2.32 |
| 0.08 | 2.12 | 3.22 | 3.46 | 3.54 | 3.56 | 3.70 |

Gain = 8

The characterization table for each Monitor Device 100 is stored in Integrated Memory 207, and CPU 203 will extrapolate the TAC reading based upon the temperature reading and the voltage reading and the gain applied.

After Monitor Device 100 has completed the reading, it will then activate the RF circuits and wait to see if an RF signal is received from Modem 104. If a signal is received from Modem 104, Modem 104 will then retrieve all of the information stored in Integrated Memory 207 and transmit it to Modem 104. If no signal is received, then Modem 104 will turn off.

Figure 3:
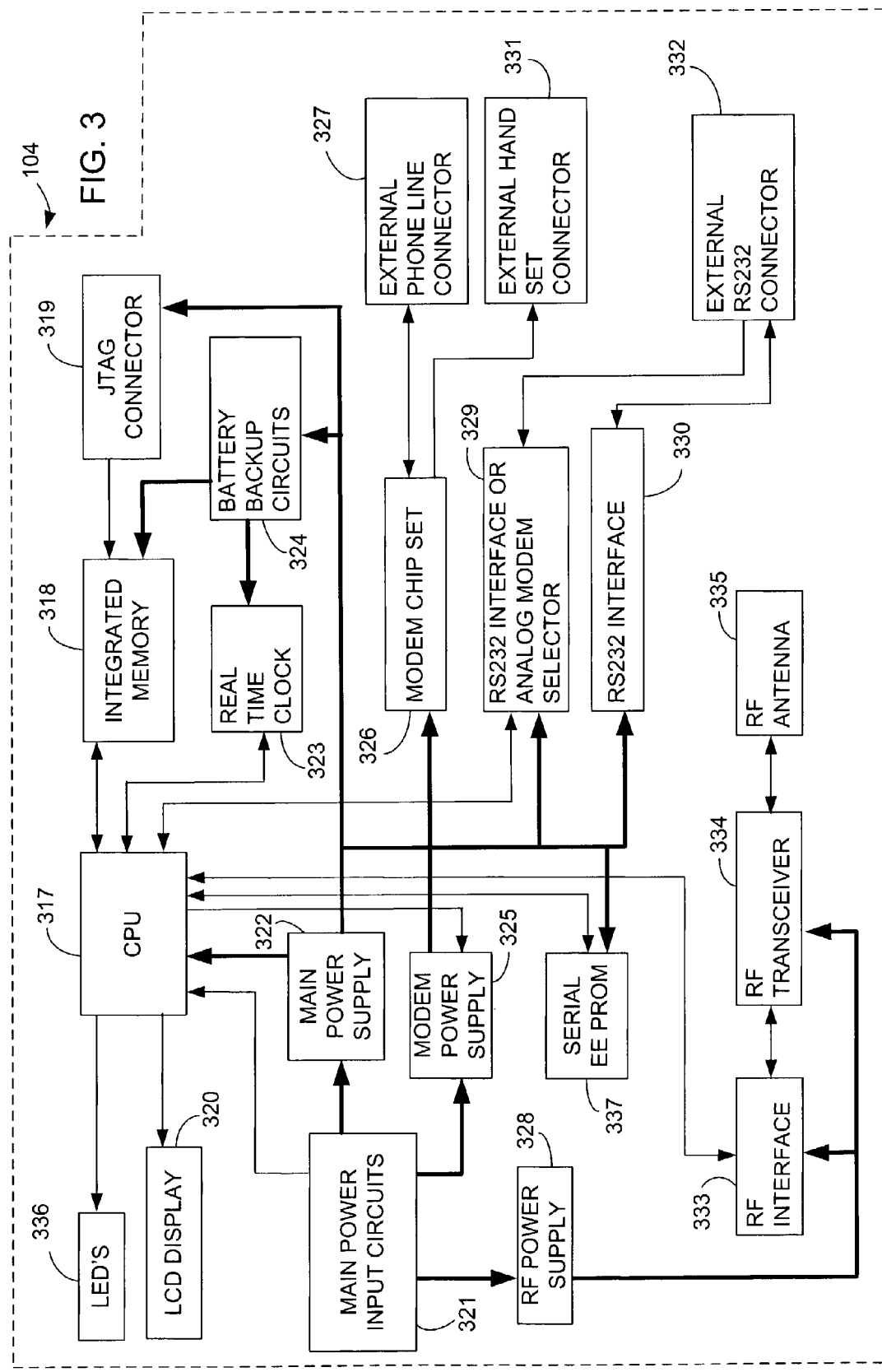
FIG. 3 shows a block diagram of the modem in an embodiment of the monitoring system of the present invention.

FIG. 3 shows a block diagram of an embodiment of Modem 104 where thicker arrows represent power circuits, and thinner arrows represent signal circuits. FIGS. 13A-13D show a top and three elevation views of an embodiment of Modem 104. Referring now to FIG. 3 and FIGS. 13A-13D, Modem 104 is powered by an external dc power supply (not shown in FIG. 3 or FIGS. 13A-13D). The dc power supply can be configured to plug into either an 115V AC supply or an international type power outlet. The dc power supply is plugged into an external power source and then plugged into the back of Modem 104 at Main Power Input 338. Main Power Input 338 is connected to Main Power Input Circuits 321. These circuits filter the power and make sure that the polarity of the power is correct and then distribute the power to Main Power Supply 322, Modem Power Supply 325, and RF Power Supply 328. Main Power Input Circuits 321 also monitor the power for AC power failures. This is accomplished by running the DC power input through a resistive divider and then into CPU 317.

Main Power Supply 322 supplies the power to CPU 317, RS232 Interface or Analog Modem Selector 329, RS232 Interface 330, Serial EE Prom 337, Battery Backup Circuits 324 and JTAG Connector 319. Battery Backup Circuits 324 supply the power to Integrated Memory 318 and Real Time Clock 323. The main power is applied as soon as Modem 104 is plugged in. The fact that Modem 104 is on is reflected by at least one LED that is illuminated in LED's 336. LCD Display 320 will also display various status messages regarding the current status of Modem 104. Tamper Tape Strip 339 is applied to a side of Modem 104 where the top half and bottom half come together as a tamper indicator. Any attempt by Subject 102 to gain access to the internal portion of Modem 104 will be evident from the altered state of Tamper Tape Strip 339.

Integrated Memory 318 is divided internally into several different memory segments. There is a small segment of the memory dedicated to the boot strap program. The boot strap program is used to initialize Modem 104 when power is first applied. The boot strap is a very basic program that will initialize CPU 317 and then check the validity of the main operating program that is stored in a larger section of Integrated Memory 318. There is also an additional RAM component that supplies extra data storage capabilities. Serial EE Prom 337 is used to store all of the critical information for Modem 104 such as the serial number, device identification information and the phone numbers that should be called to connect to Monitor Network 106. Modem 104 will retrieve and validate all of the critical information and will then validate the main operational program. If the main operational program is valid, Modem 104 will switch operation from the bootstrap program to the main operational program. Once the switch is made Modem 104 will contact Monitor Network 106 and report the latest power fail. If Subject 102 unplugs Modem 104 and moves it to a different location, or if the electricity is cut off for any reason, such as a power outage, a power fail event is recorded. If the main operational program is not valid then Modem 104 will try to contact Monitor Network 106 and get the main operational program downloaded to itself. The JTAG Connector 319 also provides a means of programming both the modem boot strap program and the main operational program into Integrated Memory 318.

To connect to Monitor Network 106, Modem 104 will check the input from the RS232 Interface or Analog Modem Selector 329 and see if there is a serial cable attached to Modem 104 at External RS232 Connector 332, which is accessible by opening up the cover of Modem 104. If there is, then Modem 104 will go into slave mode waiting for serial communications to come in through RS232 Interface 330. This mode provides a means of manually issuing commands and loading programs and or data to Modem 104. If there is no serial cable attached to Modem 104, then CPU 317 will turn on Modem Power Supply 325. After allowing Modem Chip Set 326 to power up and stabilize, CPU 317 will check for a dial tone. If no dial tone is identified, then CPU 317 will hang up and generate an alarm to indicate that the phone line is not connected at External Phone Line Connector 327. Modem 104 will then try again after a predefined delay period. External Hand Set Connector 331 receives the telephone wire that comes from the telephone hand set.

Once a dial tone has been established, CPU 317 will dial the phone number for Monitor Network 106. CPU 317 will then monitor Modem Chip Set 326 for an indication that a connection has been established with Monitor Network 106. If CPU 317 determines that the phone line is busy, or that there is no answer, then CPU 317 will hang up and log an alarm indicating that a connection could not be established. Modem 104 will then wait a predefined delay period and try to make the connection again. Once the connection is established, Monitor Network 106 becomes the master and Modem 104 becomes the slave. Monitor Network 106 will then extract all of the pertinent information that it needs to validate Modem 104 and to update its status. It will then update Real Time Clock 323 so that Modem 104 is set to the proper time for the time zone where Modem 104 is currently located. Monitor Network 106 will then upload all data that has been stored in Modem 104 since the last upload. Monitor Network 106 then has the ability to download any number of specific monitoring instructions that need to be sent to Monitor Device 100, along with all of the schedule information for Modem 104 and Monitor Device 100. Monitor Network 106 will then tell Modem 104 to hang up and start operations.

CPU 317 will hang up and turn off the power to Modem Chip Set 326. CPU 317 will then activate the RF circuits and try to establish an RF link. The RF link is established through the use of a serial to RF Transceiver 334 and the RF antenna 335. CPU 317 is connected to RF transceiver 334 through RF Interface 333 which allows the serial signal from CPU 317 to be converted to the proper voltage for the RF transceiver circuits. CPU 317 will start sending a standard message out over the RF link. This message is addressed to Monitor Device 100, so if Monitor Device 100 is within range of Modem 104 and Monitor Device 100 is active, then Monitor Device 100 will answer the message with a status message indicating that Monitor Device 100 is active and operating. Modem 104 will then become the master and Monitor Device 100 will become the slave. Modem 104 will extract all of the status information from Monitor Device 100 and will validate the operating program and any pertinent operating data needed by Monitor Device 100. Modem 104 will then update the real time clock in Monitor Device 100 so that Monitor Device 100 and Modem 104 are on the same time. Modem 104 will then extract any TAC reading information as well as any tamper or error information from Monitor Device 100. Modem 104 will then turn off the RF signal. When the RF signal is turned off, Monitor Device 100 will turn itself off and return to normal monitoring mode.

CPU 317 will then scan through the data just received and determine if any of the data needs to be sent immediately to Monitor Network 106. If not, then CPU 317 will wait a predefined delay period and then start the polling sequence again. If there is data that needs to be transmitted to Monitor Network 106 immediately, or if the time clock indicates that it is a scheduled time to call Monitor Network 106, then Modem 104 will go through the connection process and connect to Monitor Network 106.

Figure 14:
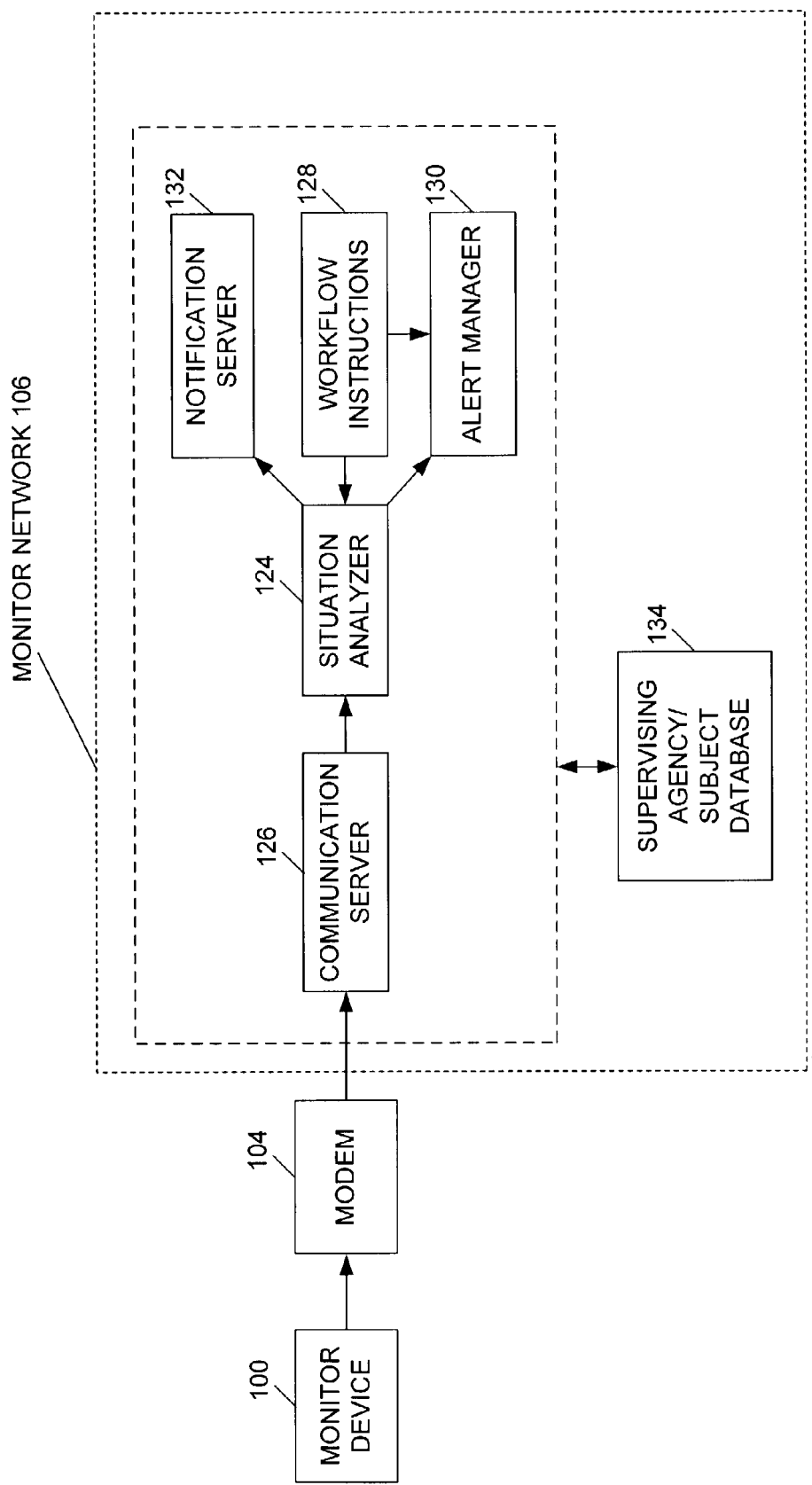
FIG. 14 shows a block diagram of the monitor network in an embodiment of the present invention.

FIG. 14 shows a more detailed block diagram of Monitor Network 106. Alert/tamper information is constantly being generated and monitored by the system components of the present invention. The following description will describe how and why the information is generated and how the information is handled and processed once it is generated.

Passive identification of Subject 102 is achieved by securely attaching Monitor Device 100 to Subject 102 in such a manner that it cannot be removed without physically damaging Monitor Device 100 and leaving evidence that Monitor Device 100 has been removed. Once Conductive Strap 18 has been adjusted and secured over Securing Pins 48, Battery Housing 16 and Battery Clip 62 are inserted into Enlarged Channel 60 securing Monitor Device 100 to Subject 102. The only way Monitor Device 100 can now be removed from Subject 102 is by cutting Conductive Strap 18 or Flexible Circuit 220, or by breaking or cutting one of Housing 12, Housing 14, Battery Housing 16, or Battery Clip 62.

When Battery 215 makes electrical contact upon being inserted in Monitor Device 100, an alert is generated indicating that power has been applied to Monitor Device 100 and the last known time and date are logged with the alert so that the duration Monitor Device 100 went without power can be determined. Normal occurrences of these alerts are generated each time Monitor Device 100 is attached to Subject 102, or each time that Battery 215 is changed in Monitor Device 100. There should never be an alert of this type generated when Monitor Device 100 is in normal operation on Subject 102. Another type of removal alarm is generated if Flexible Circuit 220 or Conductive Strap 18 are cut or disconnected at any time after Battery 215 is secured in Monitor Device 100. Monitor Device 100 will generate a Strap Alert, along with the time and date the Strap Alert was generated.

Monitor Device 100 monitors the data from Alcohol Sensor 212 and Infrared Sensor 230 combined with Temperature Sensor 210, which are mounted on Analog Board 204, to determine if there has been some type of obstruction placed between Monitor Device 100 and the skin of Subject 102. If the output of these three sensors indicates that there is an obstruction, Monitor Device 100 will log the alert along with the time and date that the alert occurred. This alert will be generated as long as the sensor data indicates that the condition is present.

All of the alerts described previously will cause Monitor Device 100 to attempt to communicate with Modem 104 as soon as possible, overriding the normal scheduled communication programmed into Modem 104 and Monitor Device 100. The system of the present invention uses the scheduled communication times to ensure that all equipment is operational under normal conditions. During normal operation there should be no reason for the equipment to override the schedules, and it will only communicate when scheduled. If no schedules were used, there would be no communication and no validation that readings were being taken and stored by Monitor Device 100. If Monitor Device 100 does not communicate at a scheduled communication time, Modem 104 will generate an alert that Monitor Device 100 failed to communicate on schedule, along with the present time and date. This alert will be labeled as a Communication Alert by Situation Analyzer 124. If Monitor Device 100 does not communicate with Modem 104 for a period of 24 hours, Modem 104 will generate a No Monitor Communication Alert, along with the present time and date. This will also be labeled as a Communication Alert by Situation Analyzer 124. Thus, the normal flow of communication between Monitor Device 100 and Modem 104 must exist or there will be alerts generated to inform the monitoring personnel that something is wrong with the system.

Modem 104 communicates with the Monitor Network 106 through Communication Server 126. The normal communication between these two devices is controlled by schedules programmed into the particular Modem 104 that is assigned to a particular Monitor Device 100. Monitor Network 106 also monitors these schedules. If Modem 104 fails to communicate when scheduled, Monitor Network 106 will generate a Communication Alert indicating that Modem 104 failed to communicate when scheduled. Thus if the normal communications cycle between Modem 104 and Communication Server 126 is broken, then alerts will be generated to inform the monitoring personnel that something is wrong with the system. This type of system architecture provides the means for equipment at each level of the communication chain to generate alarms. This guarantees that if a piece of equipment anywhere in the chain of communication fails, there will be an alarm to report it.

Data input and data management are handled by Supervising Agency/Subject Database 134. Supervising Agency/Subject Database 134 is actually a combination of databases that support all of the processes of Monitor Network 106. Supervising Agency/Subject Database 134 includes input and management of the call center data, the Supervising Agency/Subject data, and any specific information relating to a treatment center associated with the Supervising Agency 110, and the offender or patient data for all Subjects 102, including their individual monitoring and communication schedules and the device information for Modems 104 and Monitor Devices 100 assigned to them. Supervising Agency/Subject Database 134 stores all of the readings and tampers/alerts information that is received from all Modems 104 and Monitor Devices 100, as well as any device information that needs to be stored and monitored. Supervising Agency/Subject Database 134 provides a complete historical record of all readings and tampers/alerts for all Subjects 102 being monitored in the system.

Situation Analyzer 124 is used to parse the data and apply a known set of rules and instructions for handling the raw data and parsing it into a limited number of categories. These categories can be broken down as follows:

Positive TAC: Includes all positive readings and any type of positive readings that involve an interferant. An interferant is defined as a reading indicating a positive TAC, where the positive TAC is caused by some sort of topical ethanol applied to the skin or spilled/poured onto the Monitoring Device 100, but not ingested into the body by drinking.

Equipment Tamper: Includes Obstruction alarms received from Monitor Device 100. Power up alarms received from Monitor Device 100, and distance and temperature alarms that are received from Monitor Device 100. Also included are Equipment Failures.

Communication Alerts: Includes No Modem Communication, No Monitor Device Communication, Modem missed scheduled call-in time alerts, and Monitor Device missed scheduled call-in time alerts.

Equipment Maintenance: Includes alerts for scheduled maintenance, non-scheduled maintenance, and software downloads.

Equipment Assignment: Includes alerts for equipment now assigned to a client and equipment removed from a client.

Situation Analyzer 124 will make inquires to Workflow Instructions 128 to get direction on what is the default or specific action that should be applied to the message that was just received. Situation Analyzer 124 will then use those instructions and any historical data relating to similar messages to make a decision as to what to do with the message just received. Situation Analyzer 124 can also monitor historical data and escalate the severity of alert messages if there is a pattern emerging in the data that would require more immediate attention. Once Situation Analyzer 124 has made its decision, it will pass the message to Alert Manager 130. Alert Manager 130 will inquire to Workflow Instructions 128 for direction on what should be done with this message. Alert Manager 130 will then present the alert information to the monitoring personnel upon request and prompt them for some type of action required to address the alert. The main categories of alert management can be broken down as:

Review/Report the information.

Take Action: By monitoring personnel or some other person in a monitoring role.

Snooze the alert.

Log all action that is required for the alert.

Change the Status of the Alert: By taking the appropriate action the alert can now be resolved. Once resolved, the database will reflect this status and remove the Alert from the new information screens.

Situation Analyzer 124 will then check to see if the message that is being dealt with requires any type of immediate notification of a monitoring person. If it does, then Situation Analyzer 124 will send the message to Notification Server 132. Notification Server 132 will then inquire to Supervising Agency/Subject Database 134 to see what method of notification is preferred by the monitoring person, and then execute the notification method, such as sending an e-mail, sending a fax, or sending a page to the appropriate person.

Thus, the method and system of the present invention offers multiple levels of alert ranging from alerts generated by Monitor Device 100, from Modem 104, and from Monitor Network 106. The flexible and changeable scheduling at the Subject 102 level allows for more timely intervention for all of the Subjects 102 being monitored who are demonstrating problems.

Figure 4:
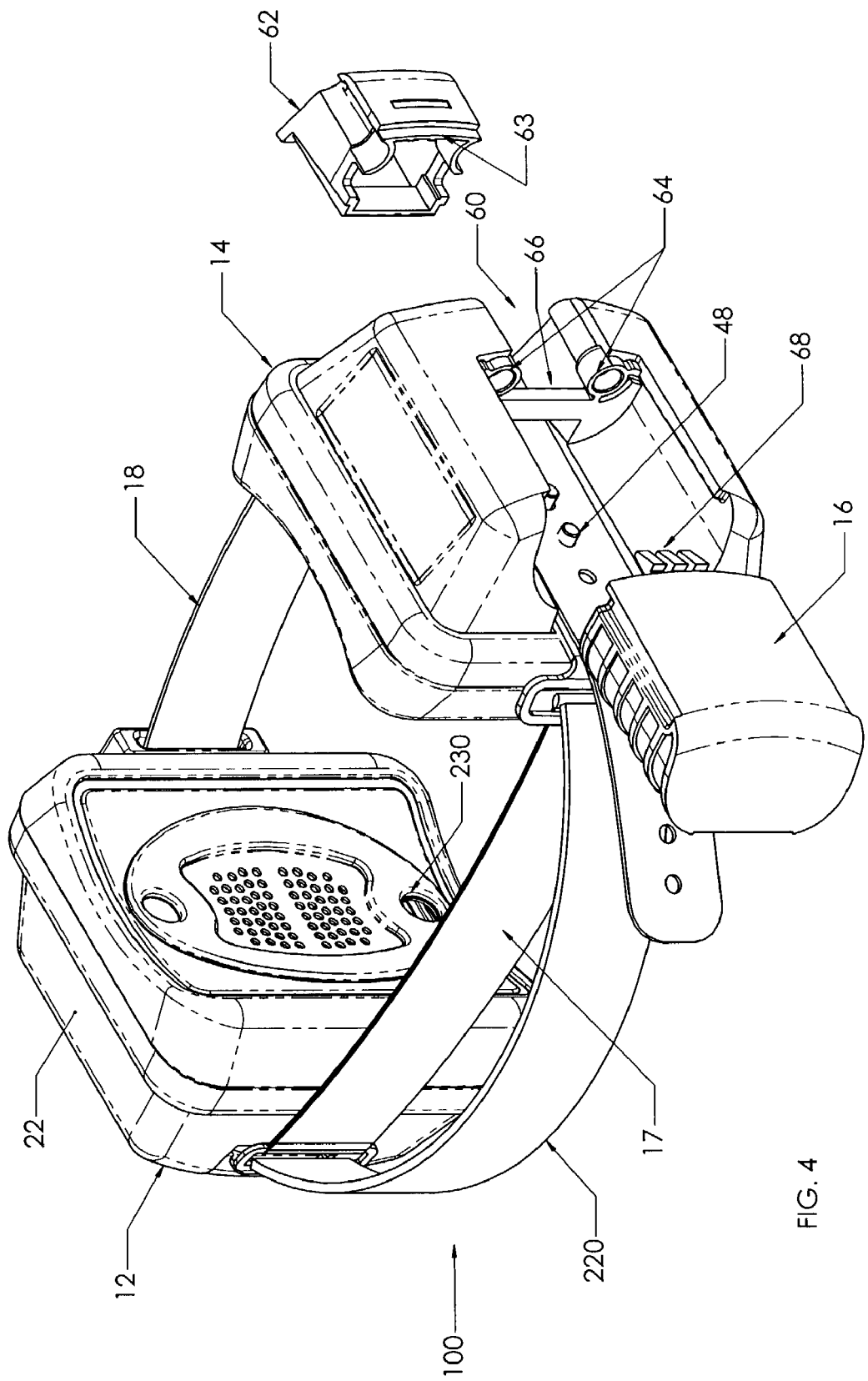
FIG. 4 shows a perspective view of a monitor device assembly in an embodiment of the monitoring system of the present invention.
Figure 5B:
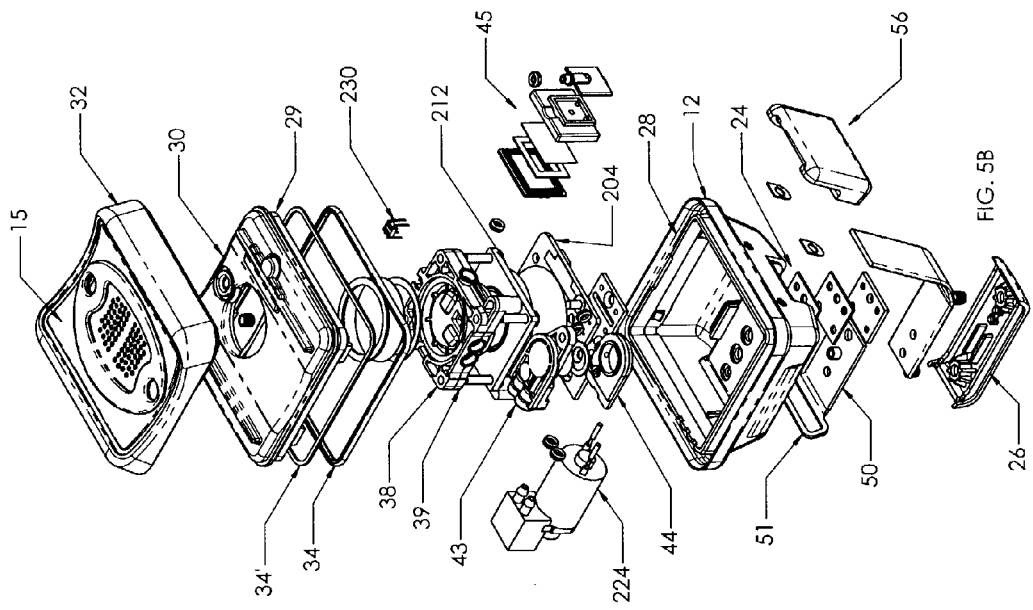
FIG. 5B shows another exploded perspective view of the analog side of the monitor device reversed 180° with respect to FIG. 5A in an embodiment of the present invention.
Figure 5A:
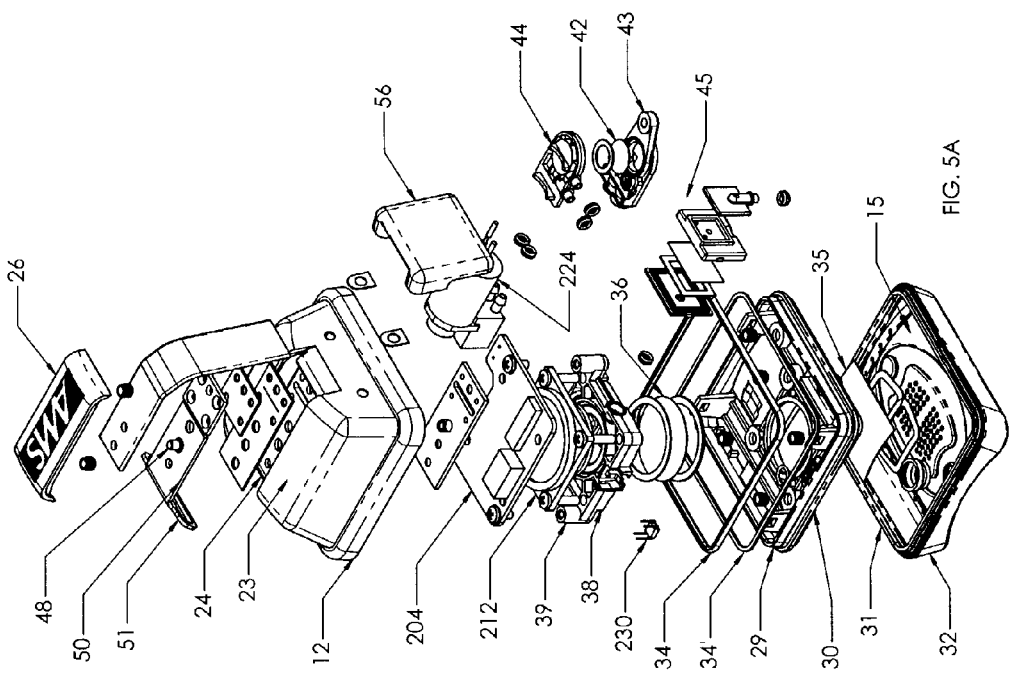
FIG. 5A shows an exploded perspective view of the analog side of the monitor device shown in FIG. 4 in an embodiment of the present invention.

Referring now to FIGS. 4, 5A, and 5*b*, a preferred form of Monitor Device 100 is illustrated for attachment to a human Subject 102, the Monitor Device 100 being in the form of a bracelet broadly comprised of an analog side having housing 12, digital side having housing 14 and Battery Housing 16, and Elastic Strap 17 with Flexible Circuit 220 connected to Conductive Strap 18 between the Housing 12 and Housing 14, all of which enable the bracelet to encircle the limb of a human Subject 102, such as an arm or a leg. Flexible Circuit 220 contains the circuit connections between Analog Board 204 in housing 12 and Digital Board 202 in Housing 14. One end of Conductive Strap 18 is connected to Flexible Circuit 220, and the other end of Conductive Strap 18 has a series of holes punched there through which are designed to fit in cooperation with Securing Pins 48 in Enlarged Channel 60 in Housing 14 so that Monitor Device 100 may be adjustably tightened to fit securely to the limb of Subject 102. Strap Securing Bracket 56 attaches to Housing 12 and channels Conductive Strap 18 towards Housing 14. Strap Securing Bracket 56 prevents Subject 102 from being able to manipulate and rotate Housing 12 and Housing 14 inside out so that Cover Plates 15 are facing outward from the skin of Subject 102. The extra rigidity provided by Strap Securing Bracket 56 along its length over a portion of Conductive Strap 18 prevents Subject 102 from being able to turn the bracelet inside out after being secured to a limb.

Housing 12 is preferably a rigid casing generally rectangular in cross-section with a concave-shaped open interior with Side Walls 22 and Back Wall 23 having a Channel 24 for mounting Elastic Strap 17, Conductive Strap 18, and Flexible Circuit 220 in a manner to be described. Cover Plate 26 is attached to Back Wall 23 so as to hold the straps permanently in place. Housing 12 is open opposite Back Wall 23 and has an outer continuous peripheral edge having Groove 28 for insertion of a Surrounding Edge 29 of an analog Base Plate 30 together with Surrounding Edge 31 of a Flexible Boot 32 in outer spaced relation to Base Plate 30. Flexible Boot 32 is of generally concave configuration, as best seen from FIG. 5B, and the same is true of a rigid metal Cover Plate 15 which is mounted centrally of Flexible Boot 32. Cover Plate 15 is curved to conform to the curvature of the leg or arm of human Subject 102 to which it is attached, and is perforated to permit the passage of air into the interior of Housing 12. Cover Plate 15 is made from surgical stainless steel so as not to cause skin irritation to Subject 102 during the duration of time of continuous wear. A D-Ring 34 and D-ring Retainer 34' are inserted into Groove 28 along with the Surrounding Edge 29 of Base Plate 30 to establish a press fit, waterproof engagement between Flexible Boot 32, Base Plate 30, and the peripheral edge of Housing 12. In this way, the assembled Base Plate 30 and Flexible Boot 32 define a Collection Chamber 33 (see FIG. 8B) for retention of each air sample recovered from the skin of Subject 102. By virtue of the flexing of Flexible Boot 32 in relation to the skin of the limb of Subject 102, a suction/vacuum created thereby helps induce the drawing of insensible skin perspiration into Collection Chamber 33 through Cover Plate 15. In this relation, a Boot Filter 35 underlies Cover Plate .15 to selectively remove any moisture from each sample as it is drawn into Collection Chamber 33. Material for Boot Filter 35 is selected to allow air to pass through but trap moisture to maintain the waterproof requirement, but allow enough air to pass through to work effectively with Pump 224.

Figure 7:
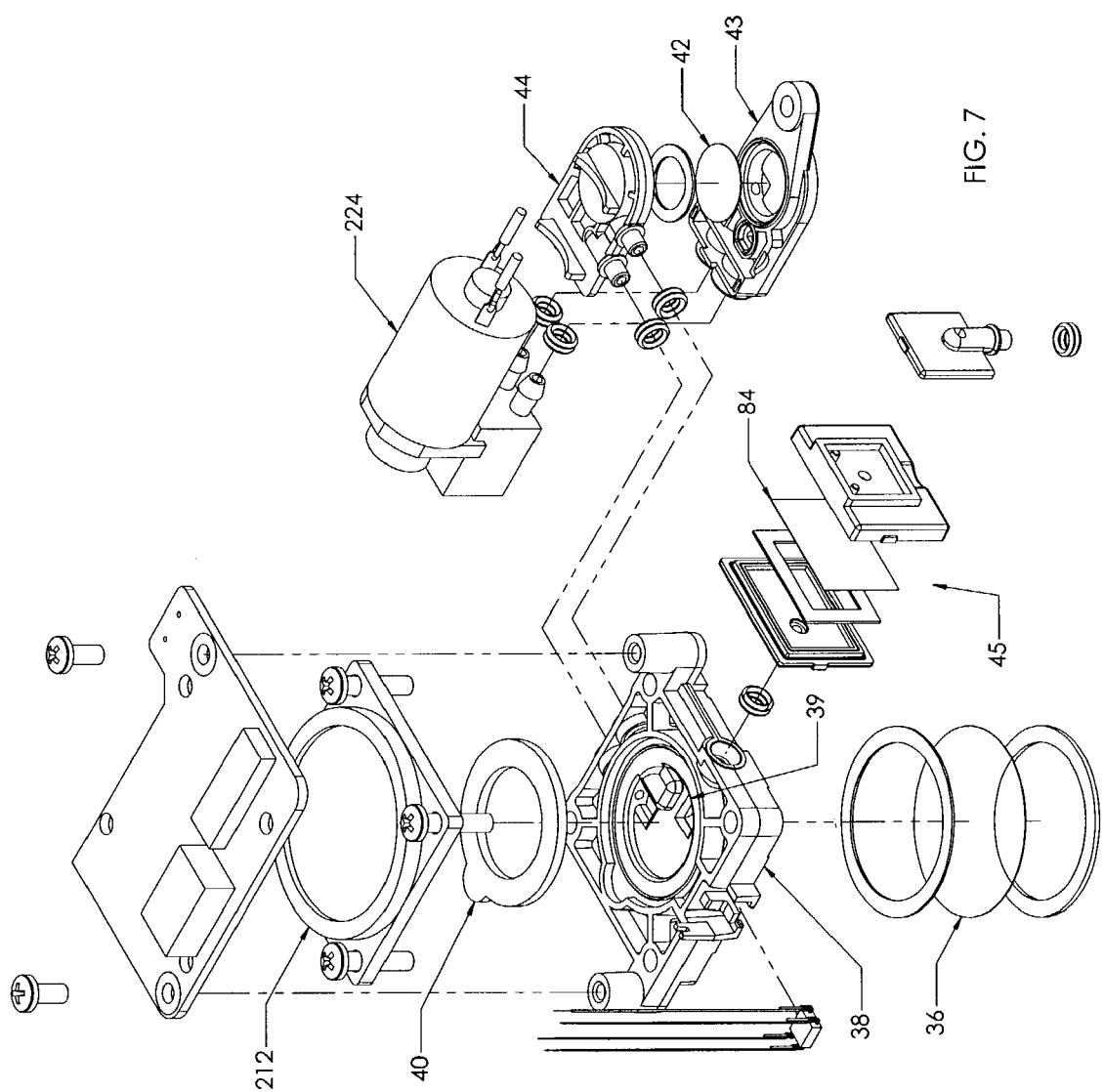
FIG. 7 shows an exploded perspective view of the sampling system in the analog side of the monitor device shown in FIGS. 5A and 5B in an embodiment of the present invention.
Figure 9D:
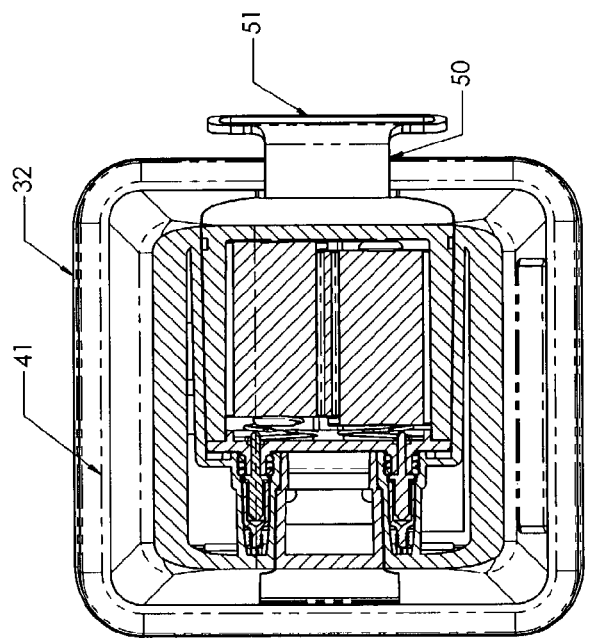
FIG. 9D shows a cross-sectional view taken about line 9D of FIG. 9C in an embodiment of the present invention.
Figure 9C:
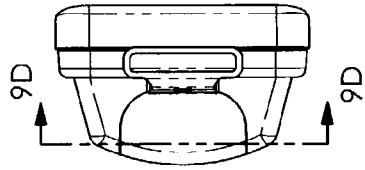
FIG. 9C shows a side view in elevation of the digital side of the monitor device shown in FIG. 4 in an embodiment of the present invention.
Figure 9A:
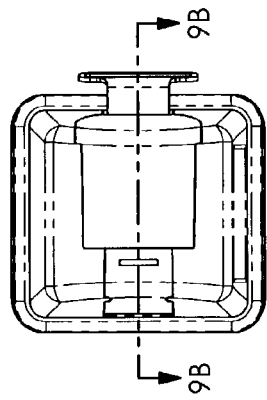
FIG. 9A shows a front view in elevation, of the digital side of the monitor device shown in FIG. 4 in an embodiment of the present invention.
Figure 9B:
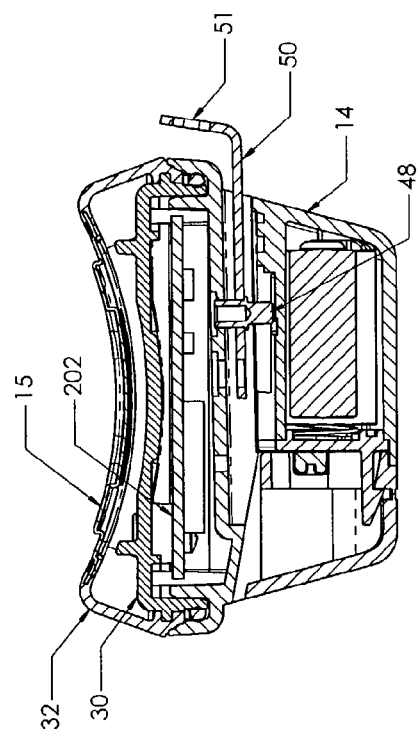
FIG. 9B shows a cross-sectional view taken about line 9B of FIG. 9A in an embodiment of the present invention.

Referring now to FIGS. 7 and 8, a Sample Chamber Filter 36 is mounted in the bottom of a First Sample Chamber 38 which is divided from a Second Sample Chamber 39 and is located directly in the path of air sample flow from Collection Chamber 33 through Base Plate 30. A Gasket 40 is mounted between Second Sample Chamber 39 and Alcohol Sensor 212. Pump 224 causes the air sample to flow from First Sample Chamber 38 through a manifold having Manifold Lower Half 43 and Manifold Upper Half 44 separated by a Moisture Filter 42, into Second Sample Chamber 39. A Check Valve Assembly 45 permits the air sample to be exhausted from Second Sample Chamber 39 into Space 52 in Housing 12. Analog Board 204 is mounted on top of Alcohol Sensor 212 and forms the bottom of Space 52. The top of Space 52 is bounded by Vent Cover 46 and Back Wall 23 in which Restraining Bracket 50 is mounted (See FIG. 5A) which has a Looped End 51 (See FIG. 5A) and Securing Pins 48. Looped End 51 has affixed to it a looped end of Elastic Strap 17. Flexible Circuit 220 is affixed to Securing Pins 48, and then extends through Restraining Bracket 50, Back Wall 23 and is electrically connected to Analog Board 204. Conductive Strap 18 is also affixed to Securing Pins 48 and then secured by Cover Plate 26.

In order to reliably measure blood alcohol content, the insensible skin perspiration which is emitted from the body in the form of vapors will migrate away from the skin and through Boot Filter 35 located on Cover Plate 15 of the analog side of Monitor Device 100. These vapors collect in Collection Chamber 33 between the Cover Plate 15 and the Base Plate 30. As this space fills with vapors from the body of Subject 102, the vapors will start to migrate through the Sample Chamber Filter 36 and collect in First Sample Chamber 38 in Housing 12. Pump 224 is activated to draw the sample from Collection Chamber 33 as well as First Sample Chamber 38 to exit into Manifold Upper Half 44 and pass through Moisture Filter 42 into Manifold Lower Half 43 and Pump 224. The sample is then forced out of Pump 224 into Manifold Lower Half 43 where it passes back into Manifold Upper Half 44 and the upper portion of Second Sample Chamber 39 and passes across Alcohol Sensor 212 where the sample will of course displace any existing air from the upper portion of Second Sample Chamber 39 through Check Valve Assembly 45. In exiting through Check Valve Assembly 45 the air is forced through another Moisture Filter 84 into Space 52 in the interior area between Second Sample Chamber 39 and Back Wall 23 of Housing 12. The sample discharged into Space 52 will in turn cause any existing air in Space 52 to migrate through Vent Cover 46 in Back Wall 23 and escape into the atmosphere.

In order to avoid false readings, it is important that the sampling system not only be waterproof to prevent the entry of moisture from the atmosphere but that any moisture in the sample itself be removed including any condensation resulting from temperature changes between the point where the sample is collected and the measuring area. From the foregoing, the filters referred to in the preceding paragraph and specifically in relation to the analog side of Monitor Device 100 are hydrophobic filters which will remove moisture from each sample while permitting the gas and entrained alcohol to pass through the air flow path as described. Thus, any moisture contained within the vapors migrating through Flexible Boot 32 will be removed by Boot Filter 35. However, as the sample undergoes cooling as it is advanced from Collection Chamber 33 through First Sample Chamber 38, Manifold Upper Half 44, and Pump 224, there will be additional condensation of moisture which must be removed in order to obtain the most accurate readings at Alcohol Sensor 212. It is equally important that Housing 12 itself be water-tight to prevent the entry of any moisture through the juncture of Flexible Boot 32 with Housing 12 as well as through the interface between Flexible Circuit 220 and Back Wall 23, and particularly from the flex circuit connection into Analog Board 204 located in the region of Vent Cover 46.

Referring now to FIGS. 6A, 6B, 9A and 9B, the digital Housing 14 is constructed in a manner closely similar to the analog Housing 12, and like parts are correspondingly enumerated. However, the interior of the housing essentially contains only a digital printed circuit, Digital Board 202, which receives the output signals of A to D Converter 236. Reed Relay 221 on Digital Board 202 can be magnetically activated to awaken the analog circuit for taking a measurement. Back Wall 58 of digital Housing 14 includes Enlarged Channel 60 for insertion of Battery Housing 16 through one end of Enlarged Channel 60 into secure engagement with Battery Clip 62, which is mounted in the opposite end of Enlarged Channel 60 between a pair of Battery Contact Sockets 64. A Cross-Member 66 is permanently mounted in Enlarged Channel 60 between Battery Contact Sockets 64 to support Housing 14. Battery Housing 16 and Battery Clip 62 are hollow and of generally rectangular configuration and correspondingly sized so that projecting catches on the ends of Tangs 68 on Battery Cover 20 will move into engagement with a molded breakaway on an off-set portion of Lip 63, on an outer end wall of Battery Clip 62 when Battery Housing 16 and Battery Clip 62 are inserted into opposite ends of Enlarged Channel 60.

Figure 12:
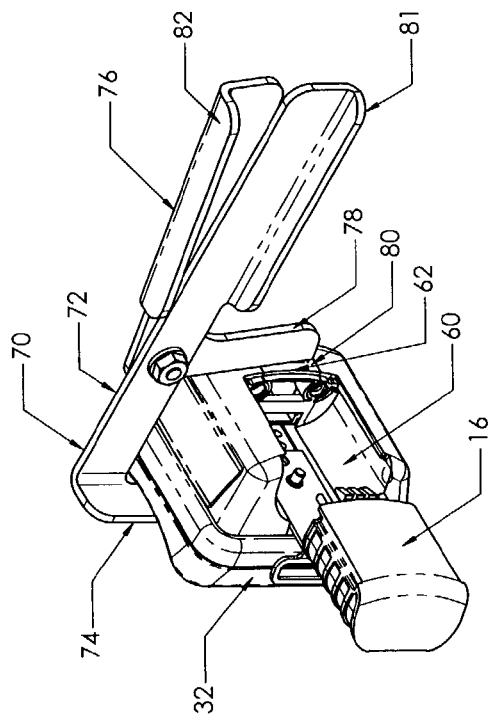
FIG. 12 shows a perspective view of the assembly shown in FIG. 11 after the battery housing has been released by the release tool in an embodiment of the present invention.
Figure 10:
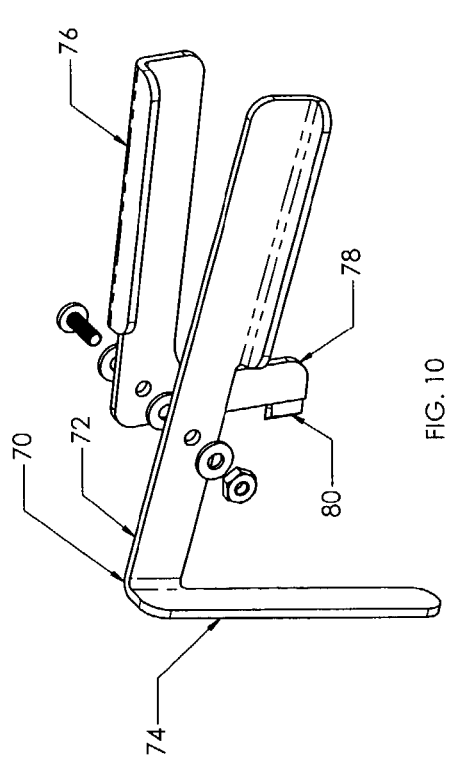
FIG. 10 shows an exploded, perspective view of the release tool in an embodiment of the present invention.
Figure 11:
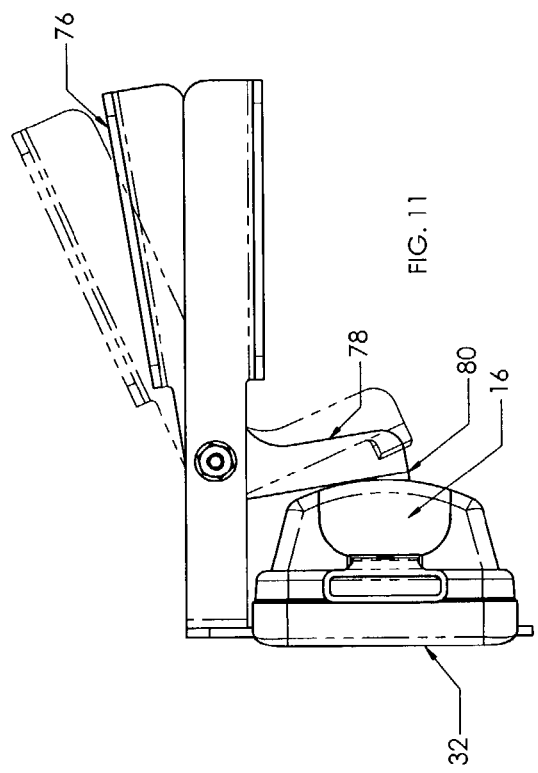
FIG. 11 shows a side view in elevation of the digital side of the monitor device shown in FIG. 4 and the release tool shown in FIG. 10 engaging the battery housing of the digital side for removal and replacement in an embodiment of the present invention.

In the preferred form, the Battery Housing 16 is designed to be permanently affixed in the Back Wall 58 of Housing 14. When thus fixed in place, it is impossible to remove Monitor Device 100 from the limb of Subject 102 without cutting Flexible Circuit 220 or Conductive Strap 18, or otherwise breaking Housing 12, Housing 14, or Battery Clip 62. Nevertheless, when it does become necessary to replace Battery 215, or simply to remove Monitor Device 100 from Subject 102, Battery Housing 16 must be removed. To this end a Release Tool 70 is provided as illustrated in FIGS. 10-12. Release Tool 70 is made up of an Elongated Handle 72 having a Stationary Arm 74 extending from one end of said arm and at right angles thereto. A tang-engaging Lever Arm 76 is pivotally connected to an intermediate portion of Elongated Handle 72 and has a Blade Member 78 with a Blade Edge 80 at its free end. Lever Arm 76 is pivotally connected to Elongated Handle 72 at a location such that when Stationary Arm 74 bears against Flexible Boot 32, Blade Edge 80 is pivoted into engagement with the molded breakaway portion of Battery Clip 62. Blade Edge 80 is movable to bear against Tangs 68 so as to release them from engagement from Battery Clip 62 and allow removal of Battery Housing 16 and enclosed Battery 215 from Housing 14 for replacement of Battery 215. It is necessary to break the breakaway portion of Battery Clip 62 in order to release Tangs 68. Battery Clip 62 must be replaced to permit reattachment of Battery Housing 16 with a new Battery 215.

In order to facilitate manual gripping of Release Tool 70, Elongated Handle 72 is provided with a Rounded Portion 81 along one edge, and Lever Arm 76 is provided with a Rounded Portion 82 along one edge which will move into engagement with an edge of Elongated Handle 72 when Lever Arm 76 is squeezed to force Blade Edge 80 into engagement with the breakaway portion of Battery Clip 62.

Having described the present invention, it will be understood by those skilled in the art that many changes in construction and circuitry and widely differing embodiments and applications of the invention will suggest themselves without departing from the scope of the present invention.

What is claimed is:

1. A system for continuous remote blood alcohol monitoring of a human subject comprising:
   a monitor device adapted to be attached to the human subject, wherein said monitor device takes a plurality of transdermal alcohol concentration readings at predetermined time intervals according to a first schedule stored in a first memory in said monitor device without active participation by the human subject, wherein said plurality of transdermal alcohol concentration readings are stored in said first memory;
   a modem in communication with said monitor device, wherein said plurality of transdermal alcohol concentration readings stored in said first memory are communicated from said monitor device to said modem at predetermined time intervals according to said first schedule through radio frequency signals without active participation by the human subject, wherein said plurality of transdermal alcohol concentration readings are stored in a second memory in said modem;

a monitor network in communication with said modem, wherein said plurality of transdermal alcohol concentration readings stored in said second memory are communicated from said modem to said monitor network at predetermined time intervals according to a second schedule stored in said second memory through a first communication link without active participation by the human subject, and further wherein said monitor network analyzes said plurality of transdermal alcohol concentration readings to determine if an alert condition exists; and a supervising agency in communication with said monitor network, wherein said monitor network communicates an alert to said supervising agency through a second communication link when said alert condition exists.

2. The system according to claim 1 further comprising:

a plurality of monitor devices each of which are adapted to be attached to one of a plurality of human subjects, wherein each of said plurality of monitor devices takes a plurality of transdermal alcohol concentration readings at predetermined time intervals according to a plurality of first schedules stored in a plurality of first memories in said plurality of monitor devices without active participation by said plurality of human subjects, wherein said plurality of transdermal alcohol concentration readings are stored in said plurality of first memories;

a plurality of modems, wherein each of said plurality of modems is paired with and in communication with one of said plurality of monitor devices adapted to be attached to said one of a plurality of human subjects, wherein said plurality of transdermal alcohol concentration readings stored in said plurality of first memories are communicated from each of said plurality of monitor devices to its paired said plurality of modems at predetermined time intervals according to said plurality of first schedules through a plurality of radio frequency signals without active participation by said plurality of human subjects, wherein said plurality of transdermal alcohol concentration readings are stored in a plurality of second memories in said plurality of modems, and further wherein each of said plurality of modems is in communication with said monitor network wherein said plurality of transdermal alcohol concentration readings stored in said plurality of second memories are communicated from said plurality of modems to said monitor network at predetermined time intervals according to a plurality of second schedules stored in said plurality of second memories through a plurality of first communication links; and a plurality of supervising agencies in communication with said monitor network, wherein each of said plurality of human subjects are associated with one of said plurality of supervising agencies, and each of said plurality of supervising agencies can access through an internet connection to said monitor network said plurality of transdermal alcohol concentration readings for each of said plurality of human subjects associated with said one of said supervising agencies.

3. The system according to claim 2 further comprising:

a monitoring station in communication with said monitor network through an internet connection, wherein said monitoring station has access to said plurality of transdermal alcohol concentration readings communicated from each of said plurality of modems paired to said plurality of monitor devices for each of said plurality of human subjects.

4. The system according to claim 3, wherein said internet connection further comprises a secure internet connection, further comprising:

a dedicated website of said monitor network, wherein said monitoring station communicates with said monitor network through said secure internet connection to said dedicated website.

5. The system according to claim 3 wherein said monitoring station communicates automatically or on a periodic basis said plurality of transdermal alcohol concentration readings communicated from each of said plurality of modems paired to said plurality of monitor devices for each of said plurality of human subjects to at least one individual at each of said plurality of supervising agencies.

6. The system according to claim 1 wherein said monitor device communicates to said modem through said radio frequency signals any tamper indicators, errors, and diagnostic data.

7. The system according to claim 6 wherein said modem, upon receiving at least one of said plurality of transdermal alcohol concentration readings, said tamper indicators, said errors, and said diagnostic data, or upon a predetermined time interval occurring, will establish said first communication link with said monitor network and communicate said at least one of said plurality of transdermal alcohol concentration readings, said tamper indicators, said errors, and said diagnostic data to said monitor network.

8. The system according to claim 6 wherein said monitor network further comprises:

a web-hosted database server for storing said plurality of transdermal alcohol concentration readings, said tamper indicators, said errors, and said diagnostic data.

9. The system according to claim 8 wherein a monitoring station and said supervising agency access said web-hosted database server through an internet connection and a secure dedicated web site.

10. The system according to claim 6 wherein said monitor network analyzes said plurality of transdermal alcohol concentration readings, said tamper indicators, said errors, and said diagnostic data into a plurality of categories, and further wherein a rules based database applied to said plurality of categories communicates an automatic alert to at least one of a call center at said supervising agency and a previously designated individual associated with said supervising agency when a rule from said rules based database is satisfied.

11. The system according to claim 10 wherein said automatic alert is one of an e-mail message, a facsimile transmission, a page to a pager, a text message, a call to a telephone, and a call to a cellular telephone.

12. The system according to claim 10 wherein said supervising agency, through said web-hosted database server through said internet connection, customizes a frequency of taking said plurality of transdermal alcohol concentration readings and customizes a method of notification for said automatic alert.

13. The system according to claim 1 wherein each of said plurality of transdermal alcohol concentration readings are time stamped by said monitor device.

14. The system according to claim 1 wherein said modem can transmit to said monitor device through radio frequency signals said first schedule comprising a monitoring schedule and a reporting schedule, and other operational information.

15. The system according to claim 1 wherein when said communication of said plurality of transdermal alcohol concentration readings from said monitor device to said modem fails at said predetermined time intervals, said monitor device repeats said communication attempt after waiting a specified time period until confirmation of transfer of said plurality of transdermal alcohol concentration readings is received from said modem.

16. The system according to claim 1 wherein when said communication of said plurality of transdermal alcohol concentration readings from said modem to said monitor network fails at said predetermined time intervals, said modem repeats said communication attempt after waiting a specified time period until confirmation of transfer of said plurality of transdermal alcohol concentration readings is received from said monitor network.

17. The system according to claim 1 wherein the continuous remote blood alcohol monitoring of a human subject is done twenty-four hours a day, seven days a week, 365 days a year.

18. A method for continuous remote blood alcohol monitoring of a human subject comprising the steps of:
    (a) attaching a monitor device to the human subject;
    (b) taking a plurality of transdermal alcohol concentration readings by said monitor device at predetermined time intervals according to a first schedule stored in a first memory in said monitor device without active participation by the human subject;
    (c) storing said plurality of transdermal alcohol concentration readings in said first memory;
    (d) communicating said plurality of transdermal alcohol concentration readings from said monitor device to a modem at predetermined time intervals according to said first schedule through radio frequency signals without active participation by the human subject;
    (e) storing said plurality of transdermal alcohol concentration readings in a second memory in said modem;
    (f) communicating said plurality of transdermal alcohol concentration readings stored in said second memory from said modem to a monitor network at predetermined time intervals according to a second schedule stored in said second memory through a first communication link without active participation by the human subject;
    (g) analyzing said plurality of transdermal alcohol concentration readings by said monitor network to determine if an alert condition exists; and
    (h) communicating an alert to a supervising agency through a second communication link when said alert condition exists.

19. The method according to claim 18 further comprising the steps of:
    attaching each of a plurality of monitor devices to one of a plurality of human subjects;
    taking a plurality of transdermal alcohol concentration readings by said plurality of monitor devices at predetermined time intervals according to a plurality of first schedules stored in a plurality of first memories in said plurality of monitor devices without active participation by said plurality of human subjects;
    storing said plurality of transdermal alcohol concentration readings in said plurality of first memories;
    communicating said plurality of transdermal alcohol concentration readings stored in said plurality of first memories from said plurality of monitor devices to a plurality of modems at predetermined time intervals according to said plurality of first schedules through a plurality of radio frequency signals, wherein each of said plurality of modems is paired with and in communication with a one of said plurality of monitor devices attached to said one of a plurality of human subjects;
    storing said plurality of transdermal alcohol concentration readings in a plurality of second memories in said plurality of modems;
    communicating said plurality of transdermal alcohol concentration readings stored in said plurality of second memories from said plurality of modems to said monitor network at predetermined time intervals through a plurality of first communication links;
    analyzing said plurality of transdermal alcohol concentration readings from said plurality of modems by said monitor network to determine if any alert conditions exist; and
    communicating a plurality of alerts to a plurality of supervising agencies through a plurality of second communication links when said alert conditions exist, wherein each of said plurality of human subjects are associated with a one of said plurality of supervising agencies, and each of said plurality of supervising agencies can access through an internet connection to said monitor network said plurality of transdermal alcohol concentration readings for each of said plurality of human subjects associated with said one of said supervising agencies.

20. The method according to claim 19 further comprising the step of:
    accessing by a monitoring station through an internet connection with said monitor network said plurality of transdermal alcohol concentration readings communicated from each of said plurality of modems paired to said plurality of monitor devices for each of said plurality of human subjects.

21. The method according to claim 20, wherein said internet connection further comprises a secure internet connection, wherein said accessing step further comprises:
    accessing by said monitoring station through said secure internet connection said plurality of transdermal alcohol concentration readings through a dedicated website of said monitor network.

22. The method according to claim 20 further comprising the step of:
    communicating by said monitoring station automatically or on a periodic basis said plurality of transdermal alcohol concentration readings communicated from each of said plurality of modems paired to said plurality of monitor devices for each of said plurality of human subjects to at least one individual at each of said plurality of supervising agencies.

23. The method according to claim 18 further comprising the step of:
    communicating by said monitor device to said modem through said radio frequency signals any tamper indicators, errors, and diagnostic data.

24. The method according to claim 23 further comprising the steps of:
    establishing said first communication link with said monitor network upon receiving at least one of said plurality of transdermal alcohol concentration readings, said tamper indicators, said errors, and said diagnostic data, or upon a predetermined time interval occurring; and
    communicating said at least one of said plurality of transdermal alcohol concentration readings, said tamper indicators, said errors, and said diagnostic data to said monitor network through said first communication link.

25. The method according to claim 24 further comprising the step of:
   storing said plurality of transdermal alcohol concentration readings, said tamper indicators, said errors, and said diagnostic data in a web-hosted database server in said monitor network.

26. The method according to claim 25 further comprising the step of:
   accessing said web-hosted database server by said monitoring station and said supervising agency through an internet connection and a secure dedicated web site.

27. The method according to claim 26 further comprising the steps of:
   analyzing by said monitor network said plurality of transdermal alcohol concentration readings, said tamper indicators, said errors, and said diagnostic data into a plurality of categories; and
   applying a rules based database to said plurality of categories; and
   communicating an automatic alert to at least a one of a call center at said supervising agency and a previously designated individual associated with said supervising agency when a rule from said rules based database is satisfied.

28. The method according to claim 27 wherein said automatic alert is a one of an e-mail message, a facsimile transmission, a page to a pager, a text message, a call to a telephone, and a call to a cellular telephone.

29. The method according to claim 27 further comprising the step of:
   customizing, by said supervising agency through said web-hosted database server through said internet connection, a frequency of taking said plurality of transdermal alcohol concentration readings and a method of notification for said automatic alert.

30. The method according to claim 18 further comprising the step of:
   time stamping by said monitor device each of said plurality of transdermal alcohol concentration readings.

31. The method according to claim 18 further comprising the step of:
   transmitting by said modem through radio frequency signals to said monitor device said first schedule comprising a monitoring schedule and a reporting schedule, and an other operational information.

32. The method according to claim 18 further comprising the step of:
   when said communication of said plurality of transdermal alcohol concentration readings from said monitor device to said modem fails at said predetermined time intervals, repeating by said monitor device said communication attempt after waiting a specified time period until confirmation of transfer of said plurality of transdermal alcohol concentration readings is received from said modem.

33. The method according to claim 18 further comprising the step of:
   when said communication of said plurality of transdermal alcohol concentration readings from said modem to said monitor network fails at said predetermined time intervals, repeating by said modem said communication attempt after waiting a specified time period until confirmation of transfer of said plurality of transdermal alcohol concentration readings is received from said monitor network.

34. The method according to claim 18 wherein steps (b) through (h) is performed twenty-four hours a day, seven days a week, 365 days a year.

* * * * *